United States Patent
Simmat et al.

(10) Patent No.: US 9,126,200 B2
(45) Date of Patent: *Sep. 8, 2015

(54) POSITIONING DEVICE FOR A SAMPLE CARRIER

(71) Applicant: Quantifoil Instruments GmbH, Jena (DE)

(72) Inventors: Olaf Simmat, Dornburg (DE); Andreas Vester, Jena (DE); Patrick Heinrich, Jena (DE)

(73) Assignee: Quantifoil Instruments GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/207,258

(22) Filed: Mar. 12, 2014

(65) Prior Publication Data

US 2014/0193312 A1 Jul. 10, 2014

Related U.S. Application Data

(63) Continuation of application No. 13/257,120, filed as application No. PCT/EP2010/053556 on Mar. 18, 2010.

(30) Foreign Application Priority Data

Mar. 18, 2009 (DE) .......................... 10 2009 013 778

(51) Int. Cl.
- *B01L 9/00* (2006.01)
- *G01N 35/04* (2006.01)
- *B01F 15/00* (2006.01)

(52) U.S. Cl.
CPC ................ *B01L 9/523* (2013.01); *G01N 35/04* (2013.01); *B01F 15/00733* (2013.01); *B01L 2200/025* (2013.01); *B01L 2300/0829* (2013.01); *G01N 2035/042* (2013.01); *G01N 2035/0491* (2013.01)

(58) Field of Classification Search
CPC ................................ B25B 5/142; B01L 9/523
See application file for complete search history.

(56) References Cited

U.S. PATENT DOCUMENTS

| 1,221,601 | A | * | 4/1917 | Rowland | ........................ 269/109 |
| 2,599,833 | A | | 6/1952 | Holmlund et al. | |

(Continued)

FOREIGN PATENT DOCUMENTS

| DE | 44 19 480 | 12/1995 |
| DE | 101 34 702 | 2/2003 |

(Continued)

OTHER PUBLICATIONS

International Preliminary Report on Patentability dated Mar. 18, 2010, issued in International Application No. PCT/EP2010/053556 (English Translation).

(Continued)

*Primary Examiner* — P. Kathryn Wright
(74) *Attorney, Agent, or Firm* — Knobbe Martens Olson & Bear LLP

(57) ABSTRACT

The invention relates to an apparatus for positioning a sample carrier plate, wherein the apparatus comprises a main body for receiving the sample carrier plate, positioning stops which are disposed in opposing first corner regions of the main body and are prestressed for clamping the sample carrier plate and mounted displaceably, an actuating device which is disposed at the main body and is equipped such that by actuating the actuating device the positioning stops can be transferred between an operating state engaging the sample carrier plate and an operating state releasing the sample carrier plate, and comprises a force transmitting element which is equipped to transmit an actuating force from the actuating device to the positioning stops.

13 Claims, 20 Drawing Sheets

(56) References Cited

U.S. PATENT DOCUMENTS

| | | |
|---|---|---|
| 6,514,465 B2 | 2/2003 | Steiner |
| 7,054,001 B2 | 5/2006 | Geiger |
| 7,070,740 B1 | 7/2006 | Matson et al. |
| 7,832,921 B2 | 11/2010 | Malin |
| 2002/0098115 A1 | 7/2002 | Fawcett et al. |
| 2003/0017083 A1 | 1/2003 | Pobering et al. |
| 2007/0020152 A1 | 1/2007 | Costello et al. |
| 2010/0218620 A1* | 9/2010 | Hoyer et al. .............. 73/863.11 |

FOREIGN PATENT DOCUMENTS

| | | |
|---|---|---|
| DE | 10 2004 021 664 | 12/2005 |
| DE | 10 2004 043 883 | 3/2006 |
| DE | 10 2010 011 899 | 9/2011 |
| EP | 1 111 391 | 12/1999 |
| EP | 1 186 891 | 9/2000 |
| EP | 1 393 797 | 8/2003 |
| EP | 1 721 964 | 5/2006 |
| GB | 1 447 643 | 8/1976 |
| WO | WO 86/0732 | 1/1986 |
| WO | WO 99/13339 | 3/1999 |
| WO | WO 99/15905 | 4/1999 |
| WO | WO 01/96880 | 12/2001 |
| WO | WO 2004/003504 | 1/2004 |
| WO | WO 2007/103963 | 9/2007 |
| WO | WO 2008/135565 | 11/2008 |
| WO | WO 2010/106147 | 9/2010 |

OTHER PUBLICATIONS

International Search Report dated May 31, 2010, issued in International Application No. PCT/EP2010/053556.

* cited by examiner

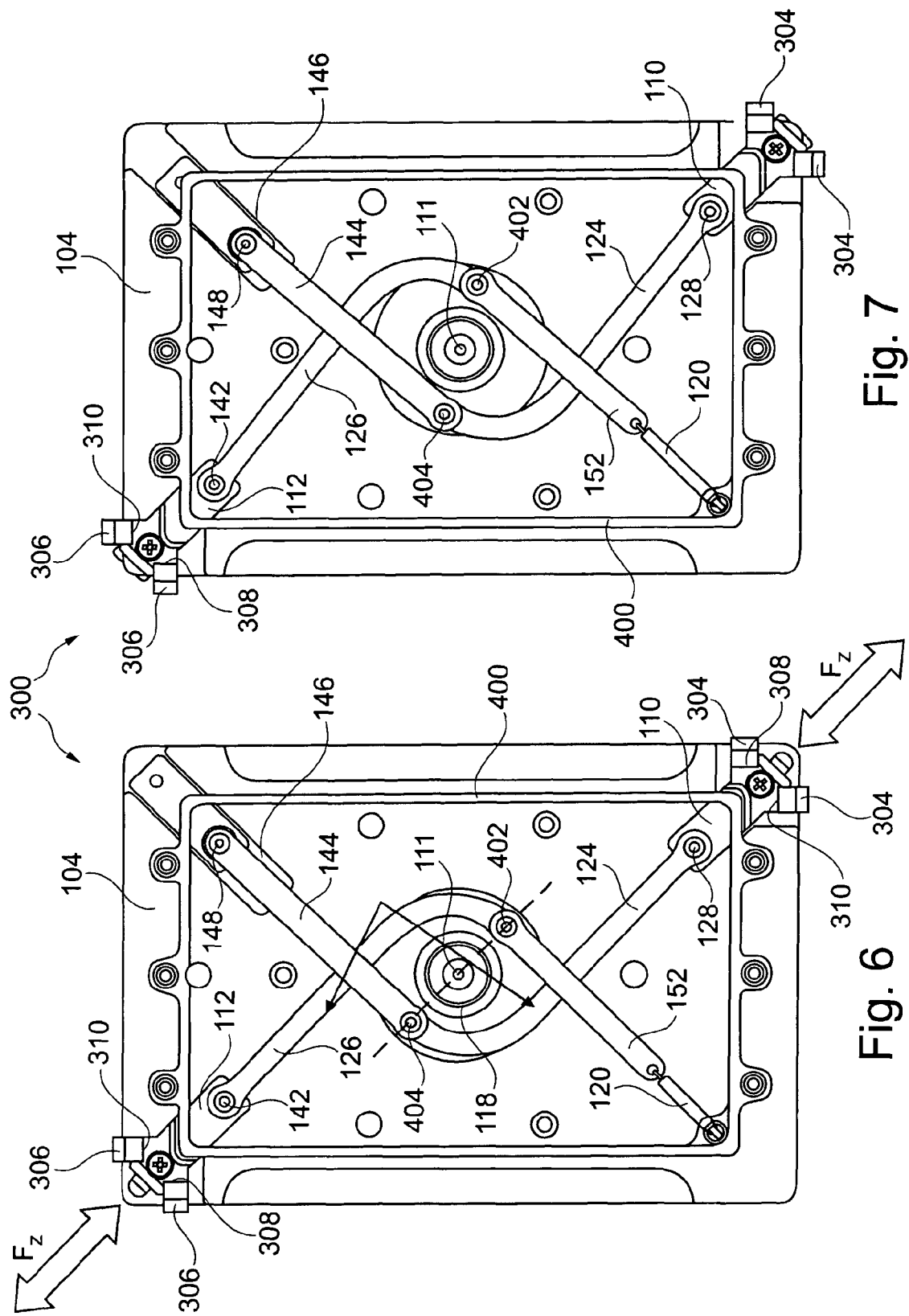

POSITIONING DEVICE FOR A SAMPLE CARRIER

RELATED APPLICATIONS

This application is a continuation of U.S. patent application Ser. No. 13/257,120, which is a U.S. National Phase of International Application No. PCT/EP2010/053556, filed Mar. 18, 2010, designating the U.S. and published on Sep. 23, 2010 as WO 2010/106147, which claims priority to German Patent Application No. 10 2009 013 778.5, filed Mar. 18, 2009. The content of each of these applications is incorporated herein by reference in its entirety.

INCORPORATION BY REFERENCE TO ANY PRIORITY APPLICATIONS

Any and all applications for which a foreign or domestic priority claim is identified in the Application Data Sheet as filed with the present application, and any and all priority claims identified therein, are hereby incorporated by reference under 37 CFR 1.57.

BACKGROUND OF THE INVENTION

1. Field of the Invention

The invention relates to an apparatus for positioning a sample carrier plate.

The invention further relates to a method for positioning a sample carrier plate.

2. Description of the Related Art

The microtiter plate has been established as standard for the simultaneous processing of a large number of small sample volumes in molecular biology. This comprises a rectangular plate of fixed dimensions, which contains a defined number of isolated cavities (wells) in rows and columns. Inside these wells different samples can be tested for their properties independently of one another. Microtiter plates having 96, 384, or 1536 wells are usually widely used in pharmaceutical, chemical, and biological research.

With increasing degree of automation and the increase in the number of wells in a microtiter plate, there is a tendency to automate filling processes and other processes. Various types of pipetting heads are known for simultaneously filling the wells, which heads can accommodate a number of pipetting tips corresponding to the number of wells.

The greater the number of wells of the corresponding microtiter plate, the smaller the diameter of each of these indentations. The requirements on the positioning accuracy of microtiter plate to pipetting head therefore increase. Furthermore, in a large number of application in pharmaceutical, chemical, and biological research it is necessary to ensure thorough mixing of the components in the wells of the microtiter plate. A simple possibility for influencing the local concentration and therefore the probability of interaction of the reaction partners is an external energy input by defined movement (shaking) of the reaction container. The advantage of such a method is the freedom from contamination as a result of the noncontact energy input (in contrast to methods using moving mixing tools). Furthermore, due to this mixing movement of a shaking apparatus, the homogenization of the temperature within the sample is also accelerated with respect to the compensating processes naturally present.

Manufacturing tolerances in the production of microtiter plates in length, width, and base height act directly on the positioning of the microtiter plate since the microtiter plate is conventionally frequently displaced by springs toward solid obstacles.

In case of conventional systems positioning pieces are often firmly attached for fixing microfilter plates during the process of pipetting and shaking. It is the object of the positioning pieces to always hold the microtiter plate in position. Springs can be contained in these positioning pieces. However, the spring force produced should be so great that the microtiter plate is held in position against the centrifugal force produced by the orbital mixing movement. Due to the high force required, the insertion of the microtiter plates into the shaking apparatus by the transporting apparatus (for example, gripper arm) of a robot can possibly be difficult or impossible. It is therefore problematical to fundamentally dispense with resilient elements since a clearance is then required in the receiving area as a result of the mentioned manufacturing tolerances (for example, ±0.5 mm), which in an unfavorable case can be 1 mm. Such a clearance allows undesirable movements of the microtiter plate during the shaking process and also conflicts with the aim of a precise positioning of the microtiter plate, in particular in the case of microtiter plates having 1536 wells, whose diameter for example is around 1 mm.

EP 1,186,891 discloses that in order to enable the spatial alignment of a support plate, this has a joint head on the underside which lies in a joint socket of a support plate. A connector of the joint head is guided through a central opening of the joint socket, which bears a clamping ring abutting against the outer side of the joint socket, which can be pressed by means of a tensile slip for fixing the alignment of the support plate. Two diagonally outwardly displaceable centering stops located opposite one another in a mirror-inverted manner on the upper side of the support plate are fastened to diagonally displaceable sliders. These engage at the opposite ends of a rotatable coupling lever with the same. This lever sits on a vertical shaft, which extends from the underside of the support plate through a hole in the joint head as far as the end of the connector. There said lever carries an actuating lever which can be rotated against the restoring force of a spiral spring for movement of the centering stops outward to allow a lowering or lifting of a microtiter plate.

WO 86/07232 discloses an apparatus for positioning a circuit panel.

EP 1,111,391 discloses a device for holding an item, in particular a microtiter plate, comprising a laying surface, where a stop limiting the displacement of the item on one side in the plane of the same is provided in the area of the laying surface, as well as a clamping apparatus having a clamping part that can be retracted with respect to the stop against a pretension.

DE 10 2004 021 664 discloses a microtiter plate shaking apparatus comprising a vibratory plate which has a reception zone for the microtiter plate and positioning pieces disposed thereon for the microtiter plate to be held. At least one positioning piece is movably mounted and can be moved between a working position and a release position. The at least one movably mounted positioning piece is movable from the working into the release position by means of a drive.

WO 99/13339 discloses a positioning apparatus for positioning a microtiter plate. A positioning platform can be provided in a surrounding platform. A further platform can be provided in the positioning platform. The surrounding platform has actuators. A movable carrier platform of the positioning platform can be moved relative to the carrier platform. In this case, bulk-like elements are disposed along the longitudinal side between the innermost further platform and the surrounded positioning platform. By means of a fluid such as compressed air, for example, the bulk-like elements can absorb fluid or blow out fluid so that a movement and positioning of the inner surrounded platform can thereby be implemented.

It is still difficult to position a sample receiving container precisely on a substrate.

SUMMARY OF THE INVENTION

It is the object of the invention to position a sample receiving container precisely on a substrate.

This object is solved by an apparatus for positioning a sample carrier plate and a method for positioning a sample carrier plate having the features according to the independent patent claims.

According to an exemplary embodiment of the present invention, an apparatus for positioning a sample carrier plate (for example, a rectangular sample carrier plate) is provided, wherein the apparatus comprises a main body (for example, a base body having a rectangular shape, on and/or in which at least a part of the remaining components of the apparatus is disposed) for receiving the sample carrier plate (for example, a base surface of the sample carrier plate), positioning stops, which are disposed in (in particular diagonally) opposing first corner regions of the main body and are prestressed (for example, with a spring force acting in a clamping manner to a midpoint of the main body) for clamping the sample carrier plate (for example, from opposite corner regions of the sample carrier plate) and mounted displaceably (for example, linearly displaceably by means of a guide rail or displaceable diagonally outward or inward with one another in some other way in a mirror-inverted manner), an actuating device (for example, an actuator device by which means an operating state of the apparatus can be set) which is disposed in a second corner region of the main body and is equipped such that by actuating the actuating device, the positioning stops can be transferred between an operating state engaging the sample carrier plate and an operating state releasing the sample carrier plate (where the positioning stops are localized in the releasing operating state further from the center with respect to the midpoint of the main body than in the engaging operating state) and a (for example, rotatably mounted) force transmitting element (for example a circular disk) which is equipped to transmit (in particular deflect or other conversion of force) an actuating force from the actuating device to the positioning stops.

The arrangement of the actuating device in a second corner region of the main body is optional. In other exemplary embodiments the actuating device can be disposed in another area of the main body, for example, along a side edge or at a certain distance from the corner region. Every feature disclosed in this description is also applicable to an exemplary embodiment in which the actuating device is not disposed in a corner region of the main body.

According to another exemplary embodiment of the present invention, a method is provided for positioning a sample carrier plate, where the method comprises receiving the sample carrier plate on a main body, clamping the sample carrier plate on prestressed and displaceably mounted positioning stops, which are disposed in opposite first corner regions of the main body, actuating an actuating device disposed in a second corner region of the main body for transferring the positioning stops between an operating state engaging the sample carrier plate and an operating state releasing the sample carrier plate, and transmitting an actuating force from the actuating device to the positioning stops by means of a force transmitting element.

A corner region of the main body can be understood in particular as a spatial position at which outer or inner edges of the main body or a carrier abut against one another at an angle, in particular substantially orthogonally (although a certain rounding in such corner regions does not need to be excluded). The corresponding component can then be disposed or be disposable spatially at or directly adjacent to such a position.

According to an exemplary embodiment, a positioning system is provided for the precise positioning of a sample carrier plate such as, for example, a microtiter plate, where the sample carrier plate can be supported from a lower side by a main body of the apparatus, can be supported in corner regions by mutually opposite positioning stops of the apparatus and the positioning stops can be moved manually or automatically by an actuating device positioned in a corner region of the main body such that this can either enable a forceless placement of the sample carrier plate on the main body without clamping action of the positioning stops or a nonpositive or positive centering of the sample carrier plate. In the latter operating state the positioning stops clearly press onto opposite corners of the, for example, rectangular sample carrier plate from two opposite directions so that this can be positioned two-dimensionally symmetrically in a predefinable manner under the influence of the clamping action. The high positioning accuracy that can be achieved with an apparatus according to an exemplary embodiment of the invention is in particular based on the fact that a central force transmission element can be disposed in a central section of the apparatus, in particular in the vicinity of a center of the apparatus, which is in operative communication with the positioning stops disposed in the opposite corner regions and the actuating device disposed in another corner region. The user can thereby undertake an actuator movement at the actuating device in a simple manner in a corner region, for example, a simple sliding movement, which sets in motion a deterministic force transmission mechanism through which the two positioning stops ultimately exert corresponding clamping forces on opposite corners of the sample carrier plate. This not only guarantees a highly accurate positioning of the sample carrier plate with respect to the apparatus but also leads to a reliable actuatability. In addition, the system is mechanically stable even when this system is to be operated with the highest precision requirement (for example, when the sample carrier plate has a plurality of liquid wells in which fluids are to be injected by means of a pipetting robot and/or when a defined shaking movement, for example, an orbital movement, is applied to the sample carrier plate for mixing the fluidic samples).

Additional exemplary embodiments of the apparatus are described hereinafter. These are also valid for the method. The apparatus can be equipped for centering the sample carrier plate with respect to a midpoint (or another predefined reference point) of the main body. For example, for automatic pipetting requirements it can be desirable to position the sample carrier plate in a spatially very precisely defined manner with respect to the apparatus so that a corresponding position signal can be transmitted to the pipetting apparatus, which enables positionally accurate pipetting or the like. According to the exemplary embodiment described, the prestress and the arrangement of the positioning stops can be configured such that in the absence of a force applied by a user, the sample carrier plate is again and again pushed back into the center of the apparatus. This is accomplished without complex alignment but can be accomplished merely by force coupling between the two positioning stops and the force transmission element as well as the actuating device while simultaneously exerting a predetermined prestress, which can act on the positioning stops.

The apparatus can in particular be equipped for positioning a microtiter plate as a sample carrier plate. A microtiter plate can be understood in particular as a laboratory device for investigating sample properties, for example, for an absorption measurement in photometers or for high throughput screening tests in pharmaceutical and plant protection research. Such a microtiter plate can comprise a rectangular plastic plate, which however can also be made of glass and other materials. Such a microtiter plate can contain many saucers or wells, which are isolated from one another, in rows and columns. Dimensions of some microtiter plates are standardized. Consequently, a standardized microtiter plate can be centered highly accurately or positioned otherwise in a predefinable manner using the positioning apparatus according to the invention, which substantially simplifies cooperation with other components (automatic pipetting apparatus or photometer arrangement).

The main body can comprise an adapter plate which can be equipped for receiving the sample carrier plate. This adapter plate can be specially adapted to a quite specific sample carrier plate. For example, a form coding of the adapter plate can correspond with a corresponding form coding of the sample carrier plate so that an incorrect placement of the sample carrier plate on the adapter plate is avoided since a form closure can be avoided in such a case.

For example, the adapter plate can be a flat adapter plate having a plane surface facing the sample carrier plate for positive receipt of a flat sample carrier plate. If the sample carrier plate has a flat base, the upper-side flat surface of the adapter plate can be provided to correspond to this sample carrier plate.

The main body can have a recess (for example, a cavity) on its surface facing the sample carrier plate, in which the flat adapter plate can be inserted so that it ends flush on an upper side and in a precisely fitting manner. Such a recess can, for example, be a substantially rectangular hole on an upper side of the main body which can be shaped and dimensioned in order to be able to precisely receive an adapter plate. After receiving the adapter plate in such a recess, the common upper-side surface of main body and adapter plate can be planar. Consequently, any tilting or incorrect positioning of the sample carrier plate on the adapter plate can be reliably avoided.

Alternatively to a flat surface, the adapter plate can have a surface structure or a topography which can be equipped for the positive receipt of a sample carrier plate having a surface structure or topography complementary to the surface structure or topography of the adapter surface. Consequently, an inverse form can be provided on the upper side of the adapter plate and on the lower side of the sample carrier plate, whereby the stability of the connection between adapter plate and sample carrier plate can be further improved. For example, such a surface structure of the adapter plate can be an arrangement of saucers having a circular cross-section, which are formed to correspond with circular projections on a lower side of the adapter plate.

The adapter plate can comprise a temperature-control unit integrated therein for controlling the temperature of a fluidic sample which can be received in the sample carrier plate. Such a temperature-control unit can, for example, be an Ohmic temperature control unit which enables a heating of the adapter plate and therefore the fluids of the sample carrier plate by means of Ohmic losses of an electric current flowing through the adapter plate. Alternatively, such a temperature control can optionally comprise a heating or a cooling, which can be achieved, for example, by means of a Peltier element. Other temperature-control systems, for example using a cooling or heating medium (for example, water) flowing through a cavity in the adapter plate can also be used. By means of such a temperature control, for example, either the temperature of a sample can be kept constant or alternatively a predetermined temperature cycle can be run through. The latter can be advantageous or desirable, for example, for PCR analyses ("polymerase chain reaction"). The temperature-control unit can be adjustable in a user-defined manner or can function independently or in a regulated manner. For example, the temperature control unit can be regulated to a certain temperature based on a temperature measured by a temperature sensor.

As a result of the various functions of the adapter plate (for example, holding, temperature control, other functions are possible), it is possible to exchange the adapter plate specially adapted to the needs of an analysis or mount it on the main body to increase the flexibility. For example, a set of several different adapter plates can be used for this purpose, which can also be mounted in the recess of the main body.

The positioning stops can be disposed exclusively in two opposite first corner regions of the main body. In other words, according to an exemplary embodiment of the invention, a first corner region of a rectangular main body can be provided with a first positioning stop and a diagonally opposite second corner region of the rectangular main body can be provided with a second positioning stop. The other two corner regions of the apparatus can then be free from corresponding positioning stops. By using precisely two corresponding and opposite pairs of positioning pieces, both a clamping of corners of the sample carrier plate and therefore a secure positioning can be achieved and also an overdetermination of positioning points can be avoided, which can then lead to an imprecise positioning of the sample carrier plate in the apparatus. Such a configuration is at the same time easy to handle and results in a low weight and small design of the apparatus.

In addition, by providing positioning stops at precisely two opposite corner regions of the main body, a type of X structure (compare FIG. 1) of the force coupling is achieved, which can be achieved by the two positioning stops and corresponding coupling rod as well as the actuating device with a corresponding coupling rod and a prestressing device with a corresponding coupling rod. This results in an efficient and very stable arrangement which can be switched between a rigid operating mode and a flexible operating mode by means of a single handle.

The positioning stops in each first corner region can be formed by means of two stop elements having two mutually perpendicular stop lines for placement on a rectangular sample carrier plate. In other word, in each corner region in which a longitudinal edge and an orthogonal transverse edge of the sample carrier plate are to be fastened, a first stop element is provided which applies a force component in a first direction to the sample carrier plate. A second stop element that generates a second force component perpendicular to the first direction can further be provided. An inner line (or an inner surface) of the respective stop element thereby rests along a, for example, straight line against the side wall surface of the sample carrier plate.

Alternatively, the positioning stops in each first corner region can be formed by means of two stop elements having a round cross-section for placement on the sample carrier plate. Such a stop element having a round cross-section can, for example, be a cylindrical pin, in particular a circular cylindrical pin, or a conical pin. A circular cylindrical pin has the advantage of a low expenditure and can clearly act with a point coupling on a corresponding point of the sample carrier plate. Conical pins have the advantage of a high flexibility and can, for example, taper toward the main body on which they can be mounted. A normal force between main body and sample carrier plate can be produced by the tapering of the conical pins toward the main body.

It is also possible to form the positioning stops as pins having a circular cylindrical section and a conical section. In particular, a section mounted on the main body can be circular cylindrical and an upper section adjoining the circular cylindrical section can be conical. This can lead to a gain in space when handling or lifting out components such as a plate, for example.

The positioning pins for clamping can be equipped, to fix microplates having different web heights. In particular, the positioning pins can be formed to support web heights of 2.5 mm, 4.0 mm, and 6.1 mm. For this purpose, the pins can be designed as pins having in particular three O-rings becoming larger toward the top, where the O rings act on the upper microtiter plate web edge. It is also possible to design the pins of solid material (for example, stainless steel) having corresponding phases and edges. The beveled edges substantially correspond to the function of the O-rings.

Consequently, the stop elements can be formed as pins having a plurality of rings of different outside diameter mounted thereon. Such rings can, for example, be made of a flexible material such as, for example, rubber. It is possible that an outside diameter of a respective ring is greater, the further away such a ring is located from the carrier element. This enables microtiter plates of different sizes to be inserted into the device.

Alternatively the stop element can be formed as pins having a plurality of steps of different outside diameter formed integrally thereon. Such steps can, for example, be fabricated as one-piece or one-material with a core of the pins. It is possible that an outside diameter of a respective step is greater, the further away such a step is located from the carrier element. This enables microtiter plates of different sizes to be inserted into the device.

Each of the positioning stops can be assigned a first linear guide element in or on which the respective positioning stop can be mounted linearly displaceably. Such a linear guide element can comprise an elongate hole along which a pin can slide in order to enable a displacement of the respective positioning stop in the direction of the centrally disposed force transmission element or away from the force transmission element. If one positioning stop moves in the direction of the center or another defined target point, the other positioning stop also moves as a result of the force coupling in the direction of the center. Conversely, one positioning stop moves away from this center when the other positioning stop is remote from this center.

The first linear guide elements can be oriented such that the positioning stops are mounted displaceably parallel to one another. This can be achieved, for example, by the linear guide grooves of the first linear guide elements being oriented substantially parallel to one another so that when they move, the positioning stops are displaced parallel to one another.

The first linear guide elements can in particular be oriented such that the positioning stops are mounted parallel displaceably offset with respect to a diagonal of the main body. In other words, according to this exemplary embodiment, the positioning stops in the first linear guide elements move parallel to one another but with a predefined lateral offset. The positioning stops then do not move exactly in the direction of a midpoint of the main body but miss the midpoint by a predefined lateral offset in the tangential direction during a continued movement. By this means a lever force can be efficiently transmitted between the force transmitting element and the positioning stops, which can lead to a rotation of the force transmitting element and therefore to an efficient force transmission.

The second corner region of the main body (in which the actuating element can be disposed) can be different from the first corner regions of the main body (in which the positioning stops are disposed). According to this exemplary embodiment there is therefore no corner region in which both the actuating element and also a positioning stop is disposed. This makes it possible to avoid undesirable interaction of these elements and leads to an advantageous transmission of force as a result of the X configuration described above. At the center of this X the force transmitting element can clearly be mounted movably to enable a lever-like force transmission with predefinable lever arm lengths.

The actuating device can have a slider for manual actuation of the actuating device by a user. Such a slider can also be guided in a second linear guide device, i.e. for example, achieved by means of a displaceable pin, which can be displaced in an elongated groove in a predefinable direction. A user is therefore protected from incorrect operation of the apparatus since such an actuating device only enables a forward or backward movement for transferring the system between the two operating states. A provision of the actuating device in a corner of the main body leads to a favorable lever arm which enables a low-force transfer of the system between the two operating states.

The slider can have a gripping piece, which can be formed in order to intuitively show a user that this is a gripping piece. For example, such a gripping piece can have an arrow-shaped end section on which the user can grip the actuating device. Both a pushing and a pulling is possible with such an arrow-shaped end section. Such a slider can, for example, be adjoined by two parallel struts which can enable a transmission of force between the gripping piece and a pin sliding in the second linear guide direction.

The actuating device can comprise a coupling piece for coupling to an electrical actuator device. According to this exemplary embodiment, an actuation of the actuating device can be made automatically by an electronic control system without requiring any intervention of a user. An electrical actuator can be provided for this purpose, which, for example, can function according to the servo motor principle.

In such an exemplary embodiment, the apparatus can comprise the electrical actuator device itself. For example, the electrical actuator device can be integrated at least partially or completely in the main body. This electrical actuator device can engage in the coupling piece for transmission of an electrical actuating force to the force transmitting element. In other words, the electrical actuator device can cooperate mechanically with the coupling piece in order to enable the transmission of a force of electrical original to the actuating element. Such a force then leads directly to a movement of the positioning stops according to a direction and an amplitude of this force.

For example, the electrical actuator device can comprise a drive shaft and a lever arm disposed thereon. The drive shaft can be equipped to be rotatable and can rotate about its own axis. A transversely projecting lever arm can be provided mounted on the drive shaft, in the end section whereof a coupling can be accomplished to a force transmitting pin or similar which can be movably disposed in a linear guide groove of the second linear guide device of the actuating element. In this way, the electrical actuating force can be efficiently transmitted. Naturally, a plurality of alternatives are possible for this embodiment.

The apparatus can further comprise an electrically controllable pipetting device, which can be equipped for pipetting a fluid into wells of the sample carrier plate. For example, a sample carrier plate can be used as a microtiter plate having 1536 wells, for example. This shows that both the number of wells or saucers and also the requirements for the positioning accuracy in such microtiter plates and similar sample carrier plates is very high. A corresponding pipetting robot can control a plurality of pipettes, each of which can pipette in or pipette out a predefined amount of a predefined substance or a substance mixture into an appurtenant well. Even with small positioning inaccuracies, this precise supply or removal of fluids in to the respective well can be negatively influenced. The positioning device according to the invention can thereby be used particularly advantageously with such an automatic pipetting device. In the case of an electronically controlled actuating device, the electronically controllable pipetting device can be controlled by the same electronic control unit (for example, a CPU, central processing unit) as the electrical actuator device. However, it is also possible that two separate control units can be used.

Alternatively or additionally to a pipetting device, the apparatus can comprise a shaking device which can be equipped for shaking the sample carrier plate mounted on the main body. While carrying out a biochemical experiment, it can be necessary or desirable that one or more components or substances poured into a respective well of the sample carrier plate are mixed with one another or are kept in mixing motion (for example, in order to avoid a phase separation). Such mixing can be achieved by means of a shaking movement. By means of the provision of the positioning stops according to the invention, a centering of the sample carrier plate relative to the apparatus can be maintained during or after a shaking movement.

For example, such a shaking apparatus can be implemented as is described in FIG. 24, FIG. 25 and the following figures of WO 2008/135565. These exemplary embodiments are included in the disclosure of this patent application by means of explicit reference, which allows the configuration of a shaking device.

In particular, according to the invention, the shaking device can be equipped for acting upon the sample carrier plate with an orbital movement (for the purpose of shaking). It is possible, for example, that one or more compensating weights is mounted on a, for example, eccentric drive shaft of such a shaking apparatus so that an uncompensated mass of the apparatus can be at least partially compensated during the shaking movement. In particular, two mutually opposite compensating weights can be disposed along the shaft. It is also possible to avoid holding together various components of the apparatus by means of magnetic elements during the shaking.

The apparatus can further comprise a mechanical (or also electrical or magnetic) prestressing device disposed in or adjacent to a third corner region of the main body, which can be equipped for transmitting a prestress (for example, a tensile prestress) to the force transmitting element. Such a prestressing device can make up the X-type force transmitting configuration of an apparatus according to one exemplary embodiment. Such a prestressing device for producing a tensile prestress can represent the apparatus in a basic setting in which a clamping force is exerted on the positioning stops as a result of the tensile stress.

The prestressing device can, for example, be a spring, in particular a helical spring, which can be fastened in the third corner region and can transmit a modified force to the positioning corners via the force transmitting element in order to initiate or terminate a clamping action. Upon actuating the clamping device, however, the system can be transferred from this clamping state into a clamping-free state from which the prestressing device can, however, exert a repelling force. A return of the system into the clamping state is thus possible with little expenditure of force.

If the prestressing device is configured as a spring, its one end can be fastened to a main body, in particular in the third corner region of the main body (for example, rigidly). The other end can be coupled to the force transmitting element. Such a spring can generate a repelling force in an elongated state whereas it can exert a forward force in a compression state.

The second corner region (in which the actuating device can be disposed) can lie diagonally opposite the third corner region (in which the prestressing device can be disposed). Consequently, all four corners of a substantially rectangular device can be provided with a corresponding functional component. These components can exert forces on one another, by making these forces act on the rotatably mounted force transmitting device which can then convert the force according to direction and/or magnitude.

In the apparatus the force-transmitting element can comprise a rotatably mounted coupling disk, which can be coupled mechanically to the actuating device and the positioning stops. A coupling disk can be understood in particular as a flat disk-like arrangement, for example having a circular base and top surface, which can be configured very flat (for example, as a force transmitting plate). A rotatably mounted coupling disk is therefore preferred since this enables a flat design and therefore a space-saving constructive form. For example, at this rotatably mounted circular coupling disk, a circle diameter can be at least three times, in particular at least five times, more particularly at least ten times as great as a cylinder height. The actuating device, the positioning stops, and optionally the prestressing element can be coupled to an upper surface of such a coupling disk, which can be mounted rotatably about a midpoint in a central section. This can have the result that a force originating from one of these elements can be transmitted to the other elements in a predefined manner. A lever arm for each element can be set to a desired higher or lower value by adjusting a radial spacing of the attachment of one of the elements to a circular surface.

A disk can be understood as the model of a flat surface supporting structure that only stresses through forces in its plane and/or bending moments about axes perpendicular to its axis. Such a disk can, for example, be implemented as a plate having circular top surfaces under a cylindrical skin surface. In other words, a cylinder can be understood as a disk whose thickness is many times smaller than its radius.

The apparatus can comprise first coupling rods, by which means a respective positioning stop can be coupled to the rotatably mounted coupling disk. The first coupling rods can be coupled in an articulated manner to the rotatably mounted coupling disk and are connected to the respective positioning stop in an articulated manner by means of a respective first linear guide. Such coupling rods can be designed as rigid elongated struts which can have articulated bearings at two end sections. At these bearings such a first coupling rod can be disposed rotatably at a positioning stop (or at a first linear guide element of a positioning stop) in an articulated rotatable manner. An opposite second end section of such a coupling rod can be mounted in an articulated manner on the rotatably mounted coupling rod. For example, such first coupling rods can be disposed near the center to an axis of rotation of the rotatably mounted coupling disk so that a relatively low lever arm acts. This can be advantageous for the transmission of force in the apparatus according to the invention.

The first coupling rods can comprise a rectilinear section and can have an adjoining bent section. The bent section can, for example, be quadrant-shaped or semicircular-shaped. An efficient deflection of force and low-wear mounting is possible by means of such a bent section. In each case, the first linear guide can adjoin the rectilinear section whereas the bent section can be guided around the rotatably mounted coupling disk, for example it can wind around a center of the rotatably mounted coupling disk along a circumferential angle of, for example, 90° or 180°.

A second coupling rod can further be provided, by which means the actuating device is coupled to the rotatably mounted coupling disk. The second coupling rod can be connected in an articulated manner to the rotatably mounted coupling disk and can be connected in an articulated manner to the actuating device by means of a second linear guide. This second elongated coupling rod can therefore be interpreted as a rotatably mounted strut on both end sections, which can enable a transmission of force between the rotatably mounted coupling disk on the one hand and the actuating device on the other hand.

According to one exemplary embodiment, the second coupling rod can be disposed radially further outward on the rotatably mounted coupling disk, in particular it can be disposed further outward than the corresponding end sections of the first coupling rods in order to allow a large rotary lever arm.

The second coupling rods can be rectilinear, i.e. can extend linearly along a predefined direction. This can be advantageous for a rigid force transmission characteristic of this second coupling rod.

One of the first coupling rods and the second coupling rods can be connected to a rotatably mounted coupling disk by means of a common connecting element (for example, a rotatable bearing). According to this exemplary embodiment, a radial distance at which the first coupling rods and the second coupling rods are coupled to the rotatably mounted coupling disk can be identical. As a result, the number of connecting elements (i.e. for example, articulated bearings) can be kept small.

The apparatus can further comprise a third coupling rod, by which means the prestressing device can be coupled to the rotatably mounted coupling disk. The third coupling rod can be connected in an articulated manner to the rotatably mounted coupling disk. By means of such a third coupling rod, a transmission of force between the prestressing device, in particular a helical spring, and the rotatably mounted coupling disk is made possible. Consequently, the prestressing of the spring can be transmitted to the rotatably mounted coupling disk. For the third coupling rod it can also be advantageous for this to act on the coupling disk radially further outward than the first coupling rods. For example, the radial distance at which the second and the third coupling rod act on the rotatably mounted coupling disk can be identical and correspond to substantially the same as the radius of the rotatably mounted coupling disk.

The third coupling rod can also be provided to be rectilinear. One length of the third coupling rod can, for example, be smaller than one length of the second coupling rod.

One of the first coupling rods and the third coupling rods can be connected to one another by means of a common connecting element on the rotatably mounted coupling disk. This again makes a simple structure possible since a small number of common connecting elements is sufficient.

In a configuration in which separate connecting elements are provided for each of the first, second, and third coupling rods for mounting on the coupling disk, these can be disposed in a coplanar manner. In other words, all the coupling rods can be disposed within a common plane which enables a flat design. Such a configuration can also reduce or minimize forces perpendicular to such a mounting plane, which can reduce the wear of the rotatably mounted elements and the coupling rods.

For example, the first coupling rods, the second coupling rods, and the third coupling rod can be mounted on a planar (for example circular) top surface of the coupling disk. In such a configuration, the lateral surface of the disk can be free from a linkage of the coupling rods. Such a configuration can be easy to mount and due to selective adjustability of a respective mounting radius of the coupling rod in relation to the rotatably mounted coupling disk, enables an adaptability of the lever arm to an associated task of the respective components. A further degree of freedom for the adjustability of the force transmission characteristic of the apparatus is thereby given.

According to one exemplary embodiment each of the first, second, and third coupling rods can be connected to an appurtenant connecting element on the rotatably mounted coupling disk. The connecting elements to the first coupling rods can be mounted radially further inward on the coupling disk than the connecting elements of the second and/or third coupling rods. This enables a planar arrangement of the coupling rods and therefore a space-saving design. At the same time, this enables a different degree of coupling forces.

The prestressing device and the actuating devices can also be mounted in a coplanar manner to one another, i.e. in the same plane. This contributes further to the flat design of the apparatus.

A secure and positionally stable mounting of microtiter plates during a pipetting process or a shaking process can thereby be rendered possible. A precise positioning and centering of the microtiter plate in relation to the carrier can be made, for example, by the centering in relation to the midpoint of the microtiter plate.

According to one exemplary embodiment of the invention, the actuating device and the force transmitting device can be coupled in such a manner that in the operating state engaging the sample carrier plate, the force transmitting element transmits a shaking force produced by the shaking device to the actuating device in such a manner that despite the action of the transmitted shaking force, the actuating device remains in a rest position with respect to a carrier element (i.e. in particular a carrier plate on which the sample carrier plate is disposed directly or indirectly) of the main body. In other words, according to such an exemplary embodiment, it can be made possible that the actuating device can be actuated for clamping or unclamping the sample carrier plate in relation to positioning stops so that in this direction of action, a corresponding force can be transmitted from the actuating device to the positioning stops. Simultaneously however, after the clamping of the positioning stops, such a coupling position of the actuating device relative to the force transmitting element can be brought about that an introduction of force leading to a movement of the actuating device in the inverse direction of action, i.e. acting on the actuating device, is mechanically blocked. This can be accomplished by deflecting a shaking force having such a direction onto the actuating device so that this is oriented orthogonally to a, for example, linear direction of displacement of the actuating device. A "direction of displacement" can be understood in this connection as an axis along which the actuating device can be displaced by a user or a robot whereas a displacement along other axes, in particular along an axis perpendicular to the direction of displacement is prevented.

In particular, the actuating device and the force transmitting element can be coupled by means of the second coupling rod in such a manner that in the operating state engaging the sample carrier plate, the second coupling rod transmits the shaking force perpendicular to the direction of displacement of the actuating device. The second coupling rod can be brought into different orientations to the direction of displacement of the actuating device. In an angular or oblique position between the second coupling rod and the direction of displacement, at least one force component different from zero can act in the direction of displacement so that a transmission of force is possible. In an orthogonal or at least substantially orthogonal (i.e. differing from a right angle by a few degrees) position between the second coupling rod and the direction of displacement, no force component (or at least none overcoming any adhesive friction) can act in the direction of displacement so that a transmission of force is blocked. Such a configuration therefore enables on the one hand a clamping of the sample carrier plate by means of low-force actuation of the actuating device and on the other hand, when the sample carrier plate is clamped, inhibits a back-transmission of a force, in particular triggered by a shaking movement of a shaking plate, to the actuating device.

An exemplary embodiment of the invention connects an orbital mixing by means of magnetic guidance to a centric clamping of a microplate. An advantageous aspect is that the centric clamping can be combined in conjunction with the shaking/mixing. During shaking the microplate should be clamped automatically in a centric manner in order to reliably hold the microtiter plate in particular for high mixing speeds or shaking speeds since the microtiter plate could otherwise be undesirably detached from the apparatus. The shaker itself always stops in its zero position, where the centric clamping aligns the microtiter plate so precisely that highly precise pipetting into the wells is made possible. Particularly in the case of 384- or 1536-well microtiter plates and well diameters becoming ever smaller, this is an important requirement for automatic pipetting. The automatic opening on the one hand allows the clamping and on the other hand the release of the plate for an exchange of the microtiter plate taking place automatically by robot gripper.

BRIEF DESCRIPTION OF THE DRAWINGS

Exemplary embodiments of the present invention are described in detail hereinafter with reference to the following figures.

FIG. 6 shows the apparatus from FIG. 3 to FIG. 5 in a closed or a microtiter plate-engaging state.

FIG. 7 shows the positioning apparatus according to FIG. 3 to FIG. 6 in an open or microtiter plate-releasing state.

DETAILED DESCRIPTION OF THE PREFERRED EMBODIMENT

The diagrams in the figures are schematic and not to scale.

The same or similar components in different figures are provided with the same reference numbers.

Figure 1:
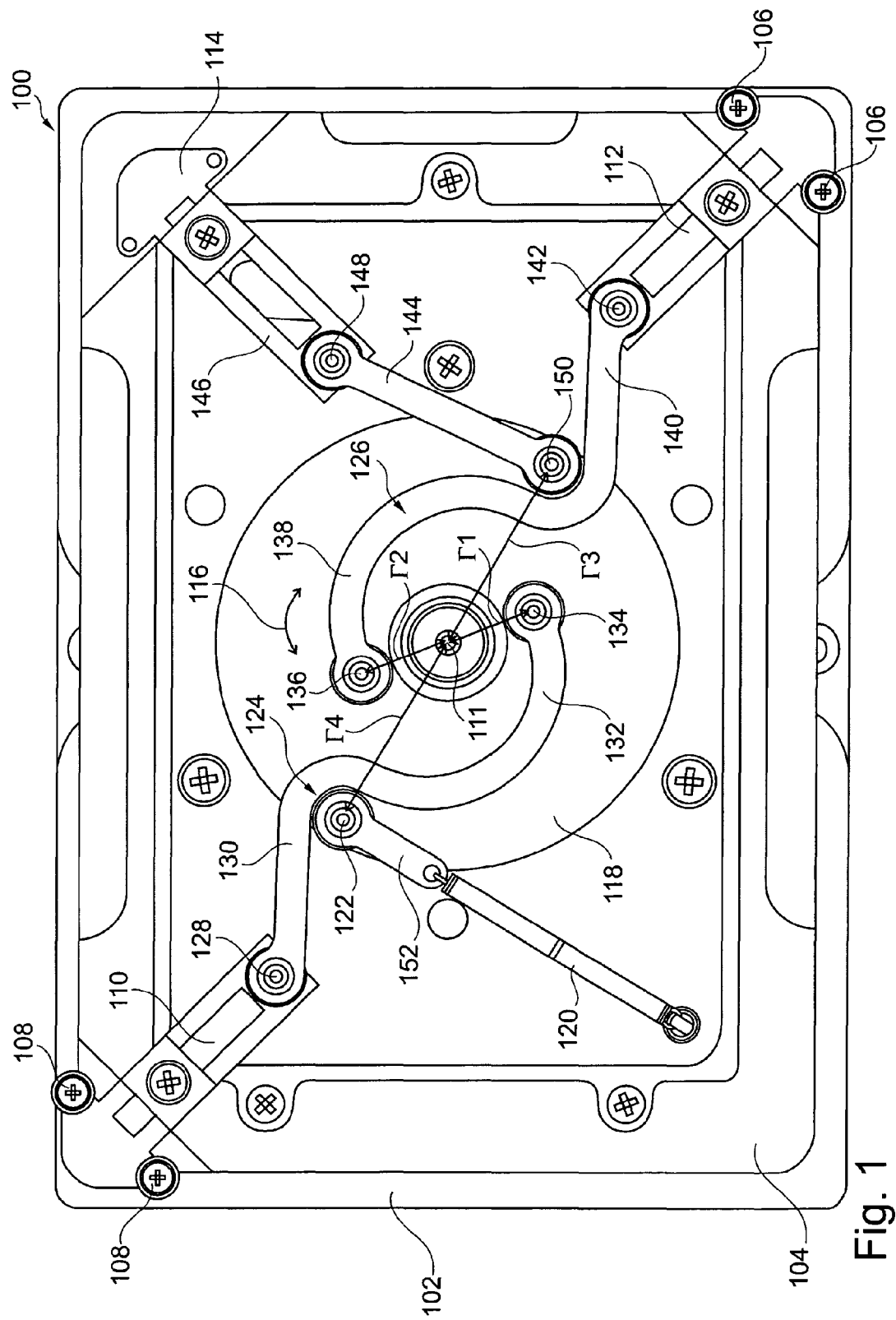
FIG. 1 shows a plan view of a positioning device according to an exemplary embodiment of the invention in an operating state in which a sample carrier plate not shown is released.
Figure 2:
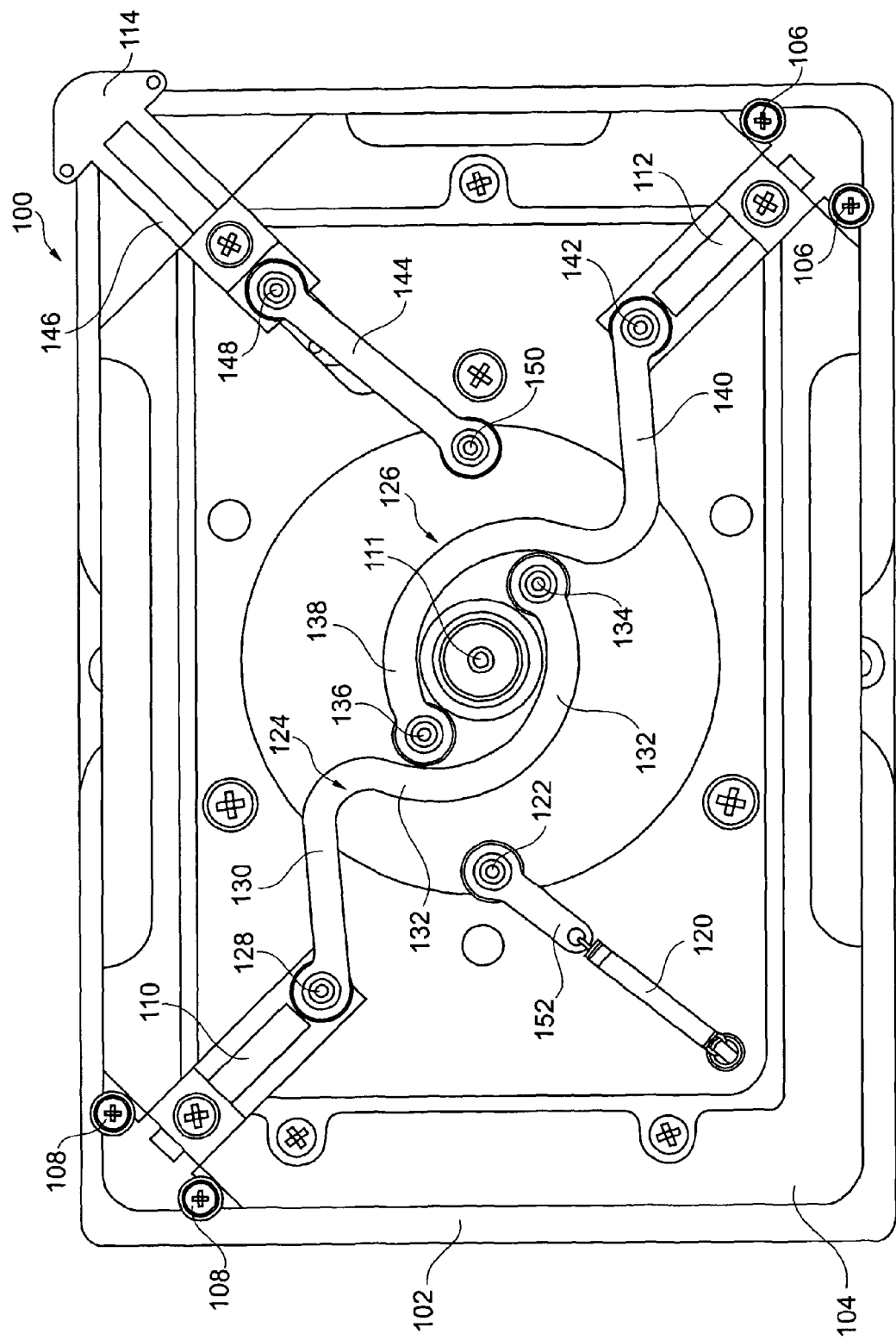
FIG. 2 shows the positioning device from FIG. 1 in another operating state in which the sample carrier plate (not shown) is engaged by the positioning corners.

With reference to FIG. 1 and FIG. 2, a sample handling device 100 according to an exemplary embodiment of the invention will be described hereinafter.

The sample handling device 100 contains a rectangular main body 102 shown in plan view, having four right-angled corner regions. A carrier 104 is provided as an elevation in a cavity in the main body 102, in which a plurality of different components of the sample handling device 100 are accommodated.

The main body 102 can contain the carrier 104. Main body 102 and carrier 104 can be formed as a common integral component or they can be formed as separable components. The main body 102 can have a fixed base housing and the carrier 104 can be mounted movably.

After the carrier 104 is mounted in the cavity of the main body 102, a recess can remain above the carrier 104 and delimited laterally by the carrier 104 of the main body 102, which can be covered by inserting an adapter plate (see, for example, FIG. 8) not shown in FIG. 1 and FIG. 2.

Two first and cooperating stop elements, designed as conical pins 108, are disposed in an upper left corner region of the carrier 104 according to FIG. 1. Two cooperating second conical positioning pins 106 which taper into the plane of the paper in FIG. 1 are mounted in an opposite corner region of the carrier 104. As is explained in detail hereinafter, the positioning stops 106, 108 are used to clamp a sample carrier plate not shown in FIG. 1, such as a microtiter plate for example.

The first positioning stops 108 are functionally operatively coupled to a first linear guide device 110. In other words, under the action of a corresponding force on the first positioning stops 108, these are displaced in the direction of a center 111 of the sample handling device 100, whereby the first positioning stops 108 slide in a groove of the first linear guide device 110.

Accordingly, the second stop elements 106 can slide in an associated linear guide device 112 so that these can either be displaced jointly with the first positioning stops 108 in the direction of the center 111 or slide jointly with the first positioning stops 108 away from the center 111 toward the corresponding corners of the carrier 104.

An actuating device 114 is accommodated in another corner region of the carrier 104, which in the exemplary embodiment according to FIG. 1 can either be actuated by hand or manually by a human user by displacing a triangular end section of the actuating device 114 in the diagonal direction in relation to the main body 102. Alternatively, the drive can be accomplished using an electrical actuator device. The latter is described in detail below.

By means of actuating the actuating device 114, the positioning stops 106, 108 can each be transferred jointly between an operating state engaging the sample carrier plate and an operating state releasing the sample carrier plate, i.e. not engaging this plate. FIG. 1 shows the released operating state in which the positioning stops 106, 108 are pushed FIG. 2 on the other hand show the engaging operating state in which the positioning stops 106, 108 are disposed closer to the center 111 of the carrier 104 than according to FIG. 1.

As can be identified from FIG. 1, the released operating state corresponds to a position of the actuating device 114 closer in relation to the center 111 than the engaging operating state according to FIG. 2, in which the arrow-like end section of the actuating device 114 projects slightly beyond the corresponding corner region of the carrier 104.

A circular disk 118 mounted rotatably, i.e. capable of rotation (see reference number 116) in the center 111 is provided as a force-transmitting element which transfers an actuating force from the actuating device 114 to the positioning stops 106, 108 in such a manner that a displacement of the positioning stops 106, 108 inward (i.e. in the direction of the center 111) or outward (i.e. away from the center 111) can necessarily be accomplished by means of displacement of the position of the actuating element 114 between the positions shown in FIG. 1 and FIG. 2.

With the sample handling device 100 it is thus possible for a microtiter plate having a substantially rectangular cross-section to be placed on the central section of the carrier 104 and directly adjoin the positioning stops 106, 108 in two opposite corner regions when the system is in the closed state according to FIG. 2. In the open state according to FIG. 1 a distance remains between the positioning stops 106, 108 and the microtiter plate.

The force transmitting mechanism described is thus used to center the microtiter plate in relation to the midpoint 111 of the carrier 104 or a fixed point of the main body 102.

As in each of the exemplary embodiments disclosed here, in the sample handling device 100 shown in FIG. 1, an optional shaking device can be integrated in the main body 102 and carrier 104 (not shown) which can be configured in such a manner that the microtiter plate executes an orbital movement between the positioning stops 106, 108 upon reception and consequently fluids contained in wells of a microtiter plate (for example, a liquid and/or a gas, with solid components not being excluded) can be reliably mixed. The clamping action of the positioning stops 106, 108 in the closed position according to FIG. 2 can hold the microtiter plate securely and centered, when averaged over time, with respect to the center 111 even during such an orbital movement.

The force transmission mechanism described cooperates with a helical spring 120 serving as a prestressing device, which is disposed in the remaining corner region of the main body 102 (see FIG. 1 and FIG. 2). Consequently, either an appurtenant positioning stop 106 or 108 or the actuating device 114 or the spring 120 is provided in each corner region of the rectangular carrier 104. This results in the X-shaped force transmission geometry shown clearly in FIG. 1, which cooperates with the rotatably mounted force transmitting disk 118 as mediator.

The helical spring 120 can be prestressed in such a manner that this transmits a tensile prestress to the rotatably mounted coupling disk 118. One end of the spring 120 is fastened to the carrier 104, with the other end being coupled via a coupling rod 152 and via a connecting element 122 to the coupling disk 118.

The sample handling device 100 comprises bent coupling rods 124 and 126. The bent coupling rod 124 couples the positioning stops 108 to the coupling disk 118. In so doing, a connecting element 128 effects an articulated connection between the linear guide device 1110 and a rectilinear section 130 of the bent coupling rod 124. A substantially semicircularly bent section 132 of the coupling rod 124 is connected in an articulated manner via a connecting element 134 to the coupling disk 118.

A distance $r_1$ between the center 111 and a center of the connecting element 134 is designated as $r_1$ in the exemplary embodiment according to FIG. 1 and is the same as the distance $r_2$ separating the connecting element 136 from the center 111. The connecting element 136 connects a bent end section 138 of the bent coupling rod 126 in an articulated manner to the circular disk 118. The bent coupling rod 126 also contains a straight section 140 which is coupled in an articulated manner via a connecting element 142 to the linear guide device 112, which is associated with the positioning stops 106.

A rectilinearly extending coupling rod 144 connects the actuating device 114, more accurately a linear guide device 146 of the actuating device 114, to the rotatably mounted coupling disk 118. For this purpose the coupling rod 114 contains a connecting element 148 for the articulated connection of the coupling rod 144 to the linear guide device 146. A connecting element 150 connects the coupling rod 144 in an articulated manner to the coupling disk 118.

Finally the further coupling rod 152 is provided which couples the helical spring 120 to the rotatably mounted coupling disk 118 in an articulated manner.

A radial distance between the center 111 and a center of the connecting element 150 is designated by $r_3$ whereas a radial distance between the center 111 and the connecting element 122 is designated by $r_4$. In the embodiment described it holds that $r_1=r_2$, $r_3=r_4$ and $r_3>r_1$.

A favorable lever system for the transmission of force is thus provided.

In the exemplary embodiment according to FIG. 1, the coupling rods 124, 126, 152 and 144 are designed as thin but rigid metal strips which are all disposed in the same plane, i.e. on an upper circular top surface of the thin disk-shaped metal body which forms a coupling surface of the coupling disk 118. A very space-saving flat design is thereby made possible.

Figure 3:
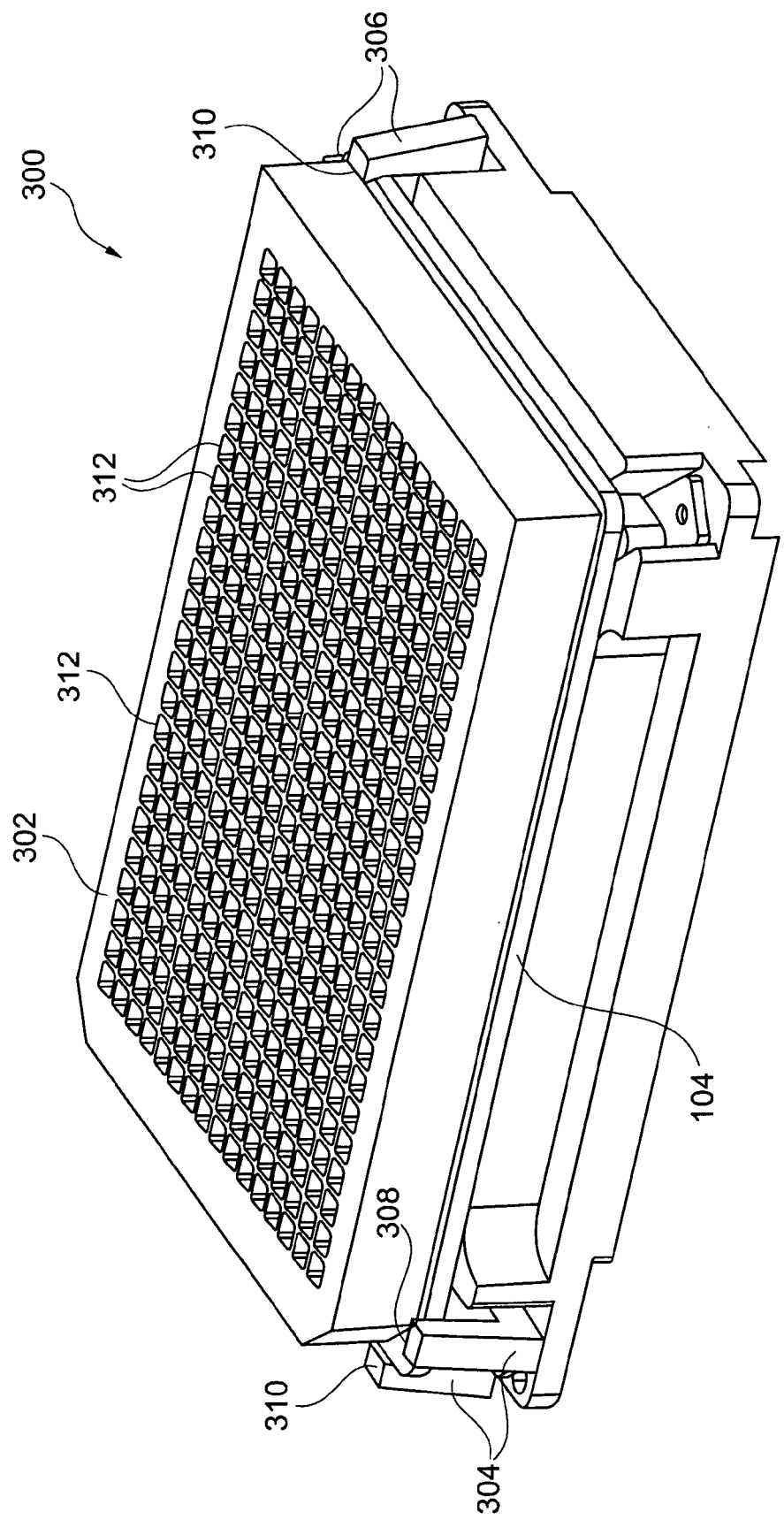
FIG. 3 shows a positioning and carrier apparatus according to another exemplary embodiment on which a microtiter plate is mounted.

FIG. 3 shows a three-dimensional view of a sample handling device 300 according to another exemplary embodiment of the invention.

In this exemplary embodiment, a microtiter plate 302 is placed on the carrier 104 and held laterally fixed. According to the exemplary embodiment of FIG. 3, this is achieved by means of stop elements 304 or 306 in opposite corner regions of the carrier 104, which nestle against side walls of the microtiter plate 302 with mutually perpendicularly disposed stop lines 308, 310 along a cohesive line. The microtiter plate 302 contains a plurality of wells or sample receiving saucers 312 arranged in a matrix shape.

Figure 4:
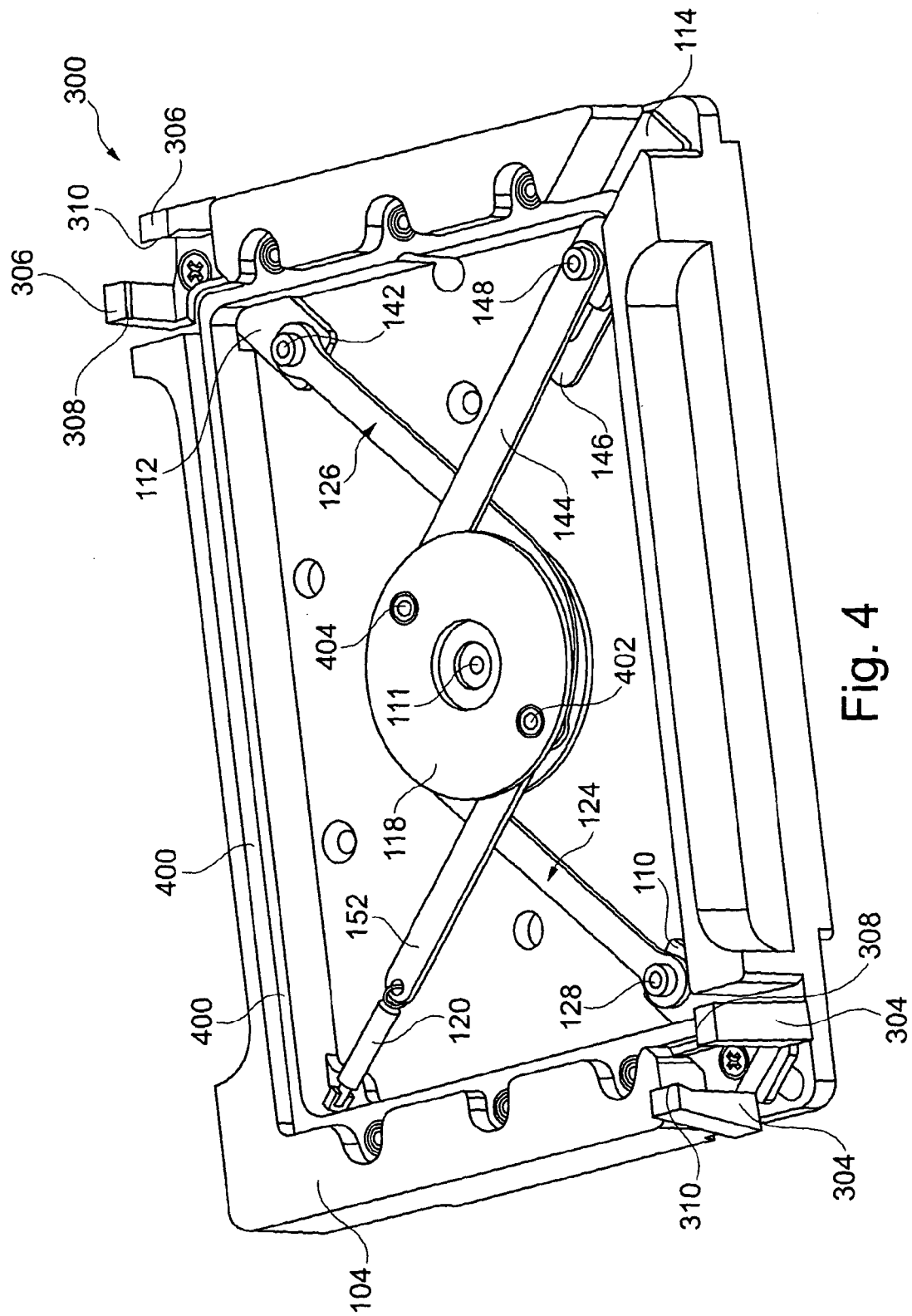
FIG. 4 shows the positioning apparatus according to FIG. 3 without cover plate and microtiter plate.

FIG. 4 shows a view of the sample receiving apparatus 300 after the microtiter plate 302 and an adapter plate disposed in a central region of the main body have been removed. This adapter plate can be mounted positively in a recess 400 and screwed, for example, and can be held with a bottom surface on a ring-like bottom section in the recess 400 and held simultaneously with side surfaces on a circumferential side wall of the recess 400.

Unlike the exemplary embodiment according to FIG. 1 and FIG. 2, in the exemplary embodiment according to FIG. 4 the various coupling rods are partially coupled to common points on the coupling disk 118, as will be described in detail with reference to FIG. 6 and FIG. 7. There it is shown in detail how the coupling rods 152, 126 are interconnected in an articulated manner by means of the connecting element 402 and the coupling rods 144 and 142 are interconnected in an articulated manner by means of a connecting element 404.

As a result of these common connecting elements 402, 404 for respectively two of the coupling rods, the coupling rods are not all laid exactly in a common plane but in two adjoining or neighboring planes. In the arrangement 300 the coupling rods 124, 126 are located further down with respect to the adapter surface than the coupling rods 152, 144.

Figure 5:
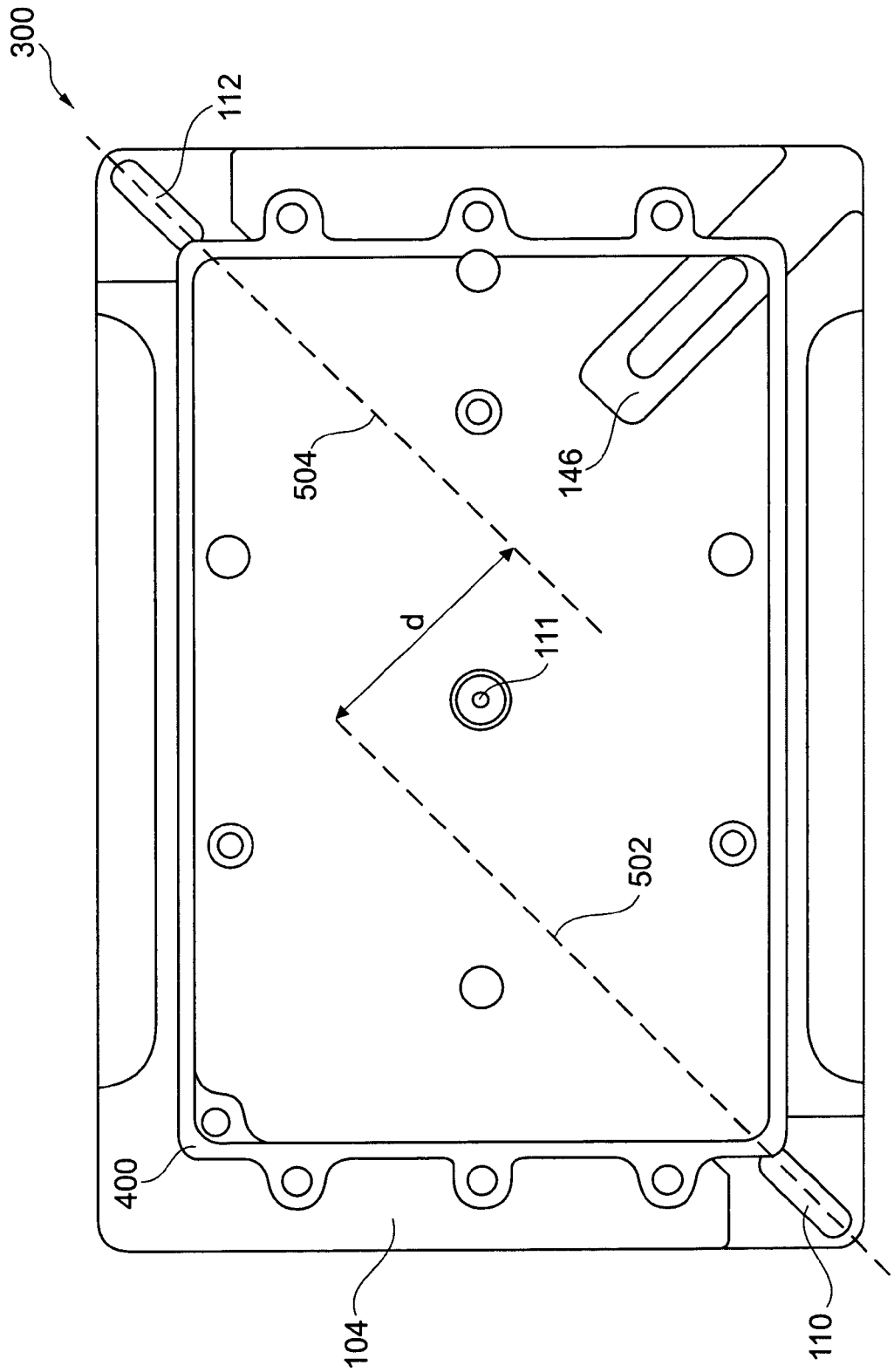
FIG. 5 shows an arrangement similar to FIG. 4 in plan view in which a rotatably mounted coupling disk, a prestressing spring and a number of coupling rods are omitted for better visibility.

FIG. 5 illustrates a view for the sample handling device 300 after a series of components shown in FIG. 4 has been dismounted.

It can be deduced from FIG. 5 in particular that a line of sight 502 of the guide groove of the linear guide device 110 is disposed parallel to a line of sight 504 of the elongate hole of the linear guide device 112. Both lines of sight 502 and 504 are disposed substantially along a diagonal of the rectangular carrier 104 and parallel to one another. They are laterally offset by a distance d with respect to one another. A particularly efficient transmission of forces is possible due to this geometry.

FIG. 6 shows a closed state and FIG. 7 shows an unlocked state of the sample handling device 300 with respect to the microtiter plate.

A functioning mode of the exemplary embodiment from FIG. 3 to FIG. 7 is described once again hereinafter.

FIG. 3 shows the microtiter plate 302 which is inserted in the positioning apparatus 300. FIG. 4 shows the mechanism which enables a positioning and fixing of the microtiter plate 302 with the carrier 104, comprising a disk 118 which is mounted rotatably with respect to the carrier 104 via a bearing. The mechanism further comprises a spring 120 fastened to the carrier and respectively two straight coupling rods 144, 152 and two partially bent coupling rods 124, 126. At their ends the coupling rods are connected on one side to the disk 118 in an articulated manner. On their respectively other side the coupling rods 124, 126, 144 are connected to the linearly guided sliders 110, 112, 146 in an articulated manner. The coupling rod 152 is connected with the second side to the carrier 104 via a spring 120. With regard to the type of connection of the bent coupling rods 124, 126 and the disk 118, see also FIG. 6 and FIG. 7. The positioning corners 304, 306 are each connected to the two sliders 110, 112.

FIG. 5 shows the structure of an exemplary embodiment of the carrier 104. Here it can be identified that the sliders 110, 112 each carrying the positioning corners 304, 306 are each guided in two linear guides which are aligned parallel to one another. A shape which projects into the linear guides is located on the sliders 110, 112 on the underside thereof.

If the slider 114 is displaced manually or automatically in the linear guide 146, this linear displacement is then transmitted via coupling rod 144 to the disk 118 which is moved against the force transmitted by the spring 120 via coupling rod 152 until the slider 146 is stopped at the stop in the associated guide groove. As a result, the sliders with the positioning pieces 304, 306 affixed thereon are displaced along the guides 110, 112 via the coupling rods 124, 126. In this position the microtiter plate 302 can be inserted into the carrier 104. When the strain on the slider 146 is released, the disk 118 is twisted by the spring force acting via coupling rod 152 and spring 120 into the initial position, whereby sliders 110, 112 and positioning pieces 304, 306 are displaced as far as the edge of the base of the microtiter plate 302. The open and closed state of the mechanism is shown in FIG. 6 or FIG. 7.

During an orbital shaking movement, a centrifugal force having a circulating direction of action acts on the microtiter plate 302 and the liquids contained therein. Since however, the positioning pieces 304, 306 are guided linearly on the sliders 110, 112, only one possible degree of freedom of the movement is obtained as a result of the centrifugal force, which is represented by the indicated arrows in FIG. 6.

A fundamental improvement of the mechanism compared with conventional systems is that the articulation point of the coupling rods 124, 126 is positioned on the rotatably mounted disk 118 in the closed state such that a very low effective lever arm, ideally lever arm=0, is obtained with respect to the pivot point of the disk 118. This has the result that due to the centrifugal force, a very small torque is exerted on the disk 118 whereas the effective lever arm of the prestressed spring 120 on the disk 118 is large and in this exemplary embodiment corresponds to the pitch circle radius of its linkage.

As a result, the advantage is obtained in particular that a very rigid connection of positioning piece 304, 306 and microtiter plate 302 can be achieved with a very small spring force. Despite this rigid connection, in the opened state the mechanism can be equipped with the microtiter plate 302 in forceless manner. Another advantage of this mechanism lies in the centering of the microtiter plate 302 with regard to the carrier 104. The manufacturing tolerances of length and width of the microtiter plates 302 therefore do not influence the position of the wells in relation to the center of the carrier 104.

Figure 8:
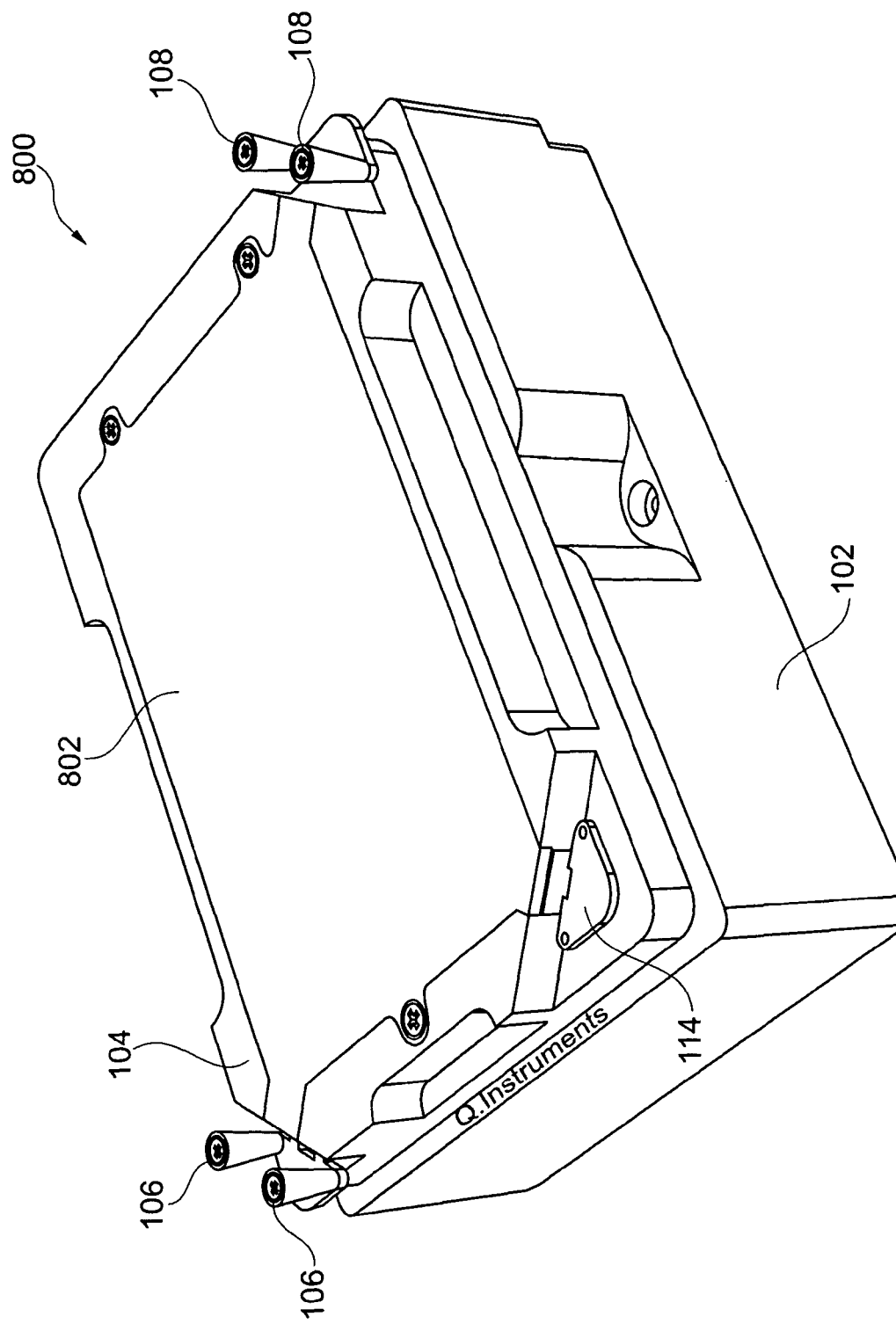
FIG. 8 shows a positioning apparatus according to another exemplary embodiment of the invention without mounted microtiter plate and with adapter plate in place.

FIG. 8 shows a sample handling device 800 according to another exemplary embodiment of the invention in which an adapter plate 802 is inserted in the recess 400.

As shown in FIG. 8, the adapter plate 800 ends flat with an adjoining surface region of the carrier 104.

Figure 9:
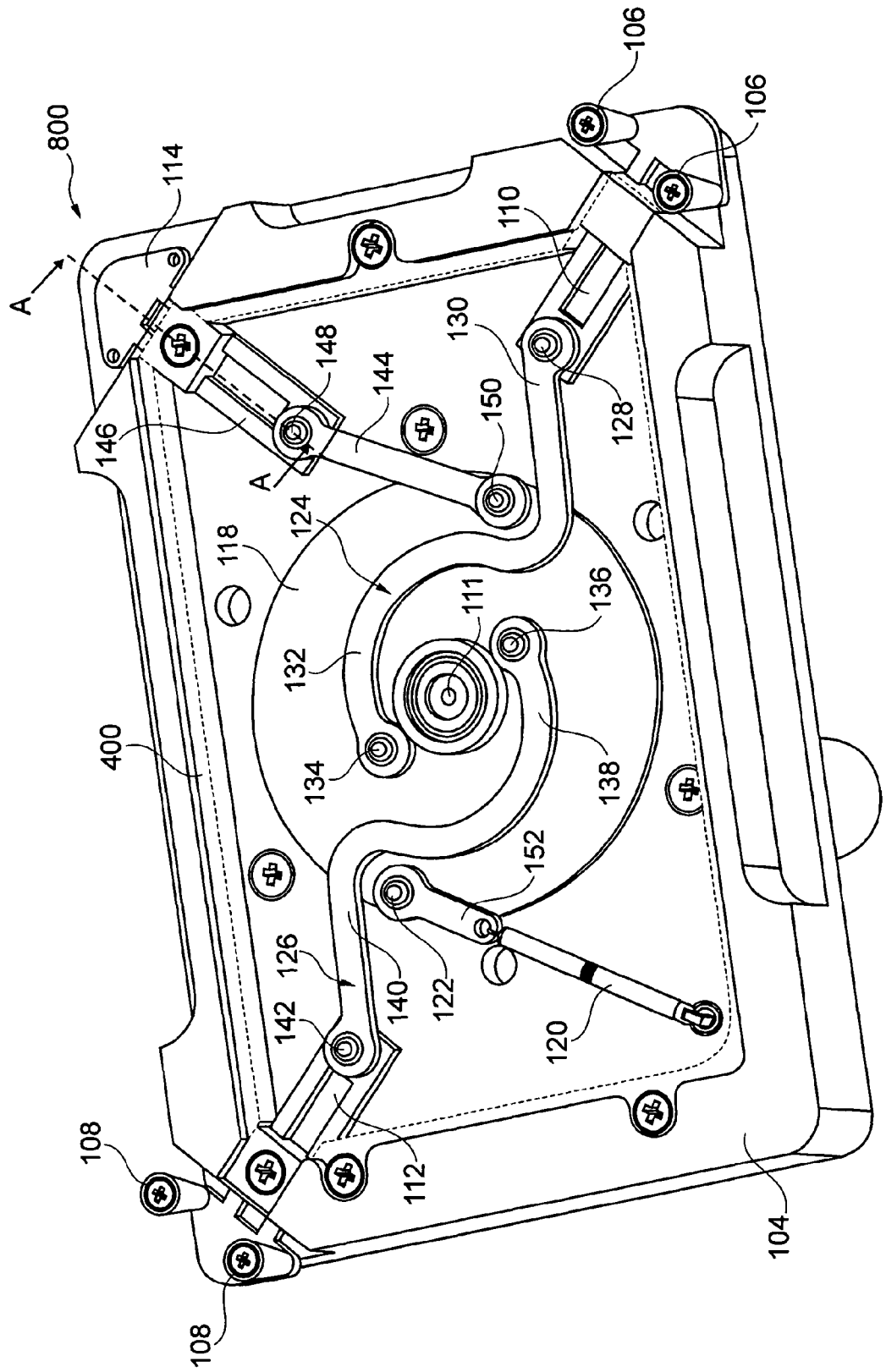
FIG. 9 shows the positioning apparatus according to FIG. 8 in plan view after removing the adapter plate.

FIG. 9 shows the sample handling device 800 after removing the adapter plate 802 in which, for example, a temperature control unit can be introduced for controlling the temperature of a microtiter plate (not shown).

Figure 10:
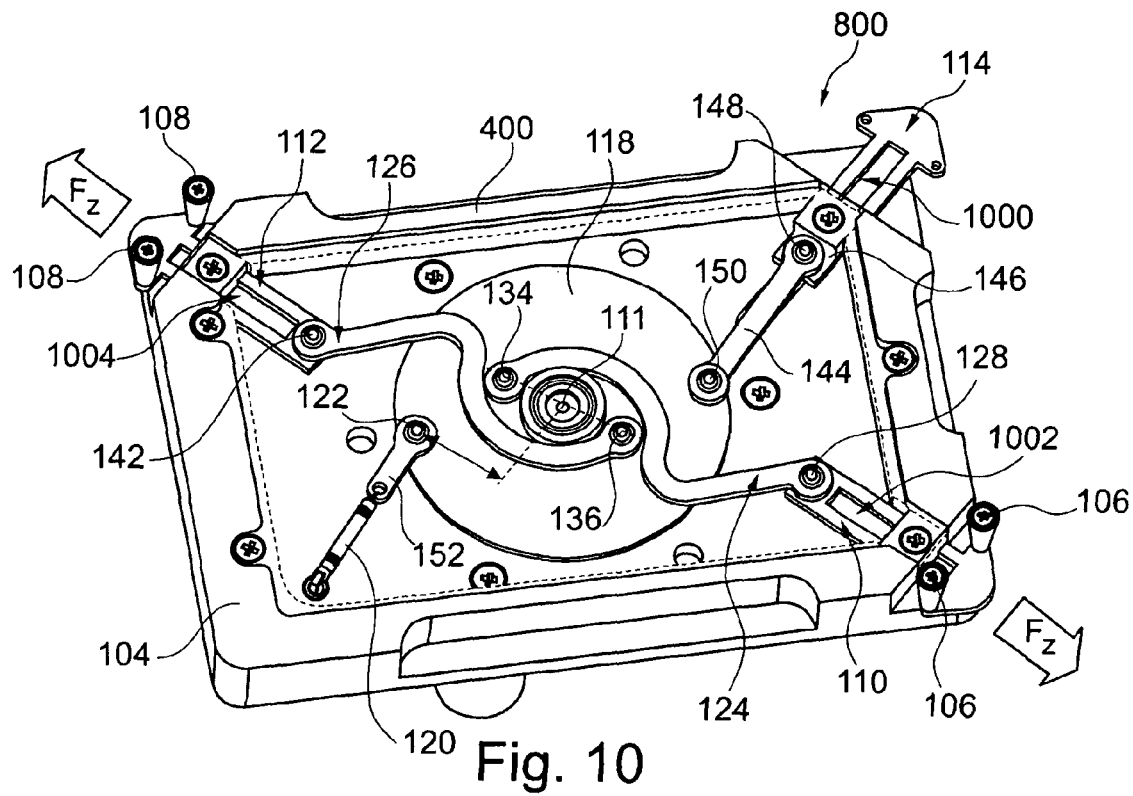
FIG. 10 shows the positioning apparatus according to FIG. 8 or FIG. 9 in the alternative operating state to FIG. 9.

FIG. 9 shows the non-engaging operating state and FIG. 10 shows the engaging operating state of the sample handling device 800.

Figure 11:
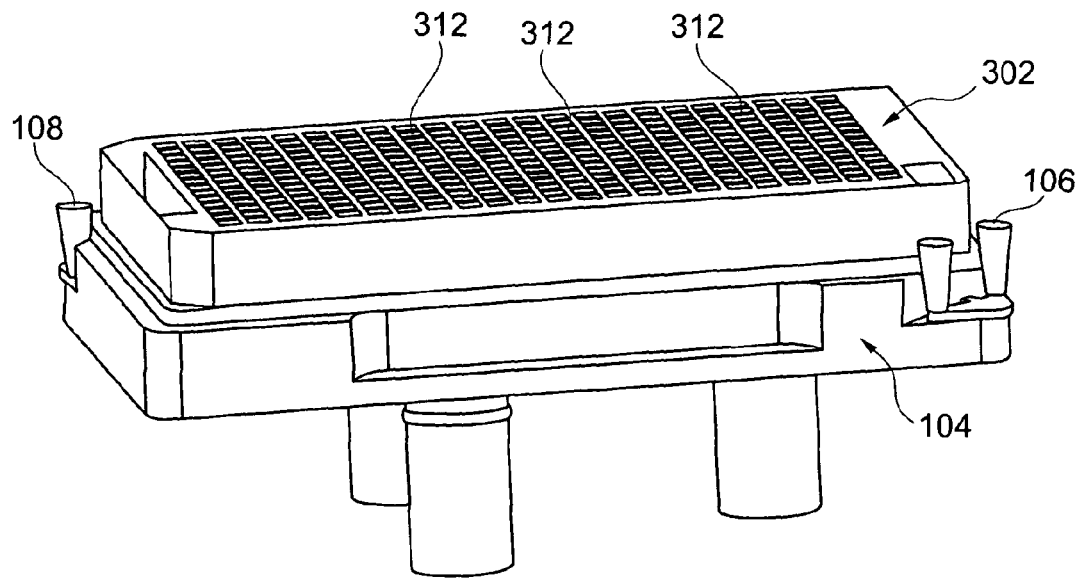
FIG. 11 shows the positioning apparatus according to FIG. 8 to FIG. 10 with microtiter plate in place.

In FIG. 11 the microtiter plate 302 is received on the adapter plate 802.

A functioning mode of the exemplary embodiment from FIG. 8 to FIG. 11 is described once again hereinafter.

FIG. 11 shows the microtiter plate 302 which is inserted in the positioning apparatus 800. FIG. 8 to FIG. 11 further shows the mechanism which enables a positioning and fixing of the microtiter plate 302. This consists of a carrier plate, a disk 118 which is mounted rotatably with respect to the carrier 104 via the bearing 112. The mechanism further comprises a spring 120 fastened to the carrier and respectively two straight coupling rods 144, 152 and two partially bent coupling rods 124, 126. At their ends the coupling rods are connected on one side to the disk 118 in an articulated manner. On their respectively other side the coupling rods 124, 126, 144 are connected to the linearly guided sliders 110, 112, 146 in an articulated manner. The linear guidance is achieved via T-groove blocks (relevant guide slots 1002 and 1004 are shown in FIG. 10). The coupling rod 152 is connected with the second side to the carrier 104 via a spring 120. Two conical pins 106, 108 are attached to each of the two sliders 110, 112, by which the microtiter plate 302 is centered and fixed non-positively. If the slider 114 is linearly displaced, manually or automatically, this linear displacement is then transmitted via coupling rod 144 to the disk 118 which is moved against the force transmitted by the spring 120 via coupling rod 152 until the slider 146 is stopped at the stop in the associated guide groove 1000. As a result, the sliders 110, 112 with the positioning pieces 106, 108 affixed thereon are displaced along the guides 1002, 1004. In this position the microtiter plate 302 can be inserted into the mechanism. When the strain on the slider 114 is released, the disk 118 is twisted by the spring force acting via coupling rod 152 and spring 120 into the initial position, whereby sliders 110, 112 and conical pins 106, 108 attached thereto are displaced as far as the edge of the base of the microtiter plate 302. The open state is shown in FIG. 9 and the closed state of the mechanism is shown in FIG. 10.

During an orbital shaking movement, a centrifugal force having a circulating direction of action acts on the microtiter plate 302 and the liquids contained therein. Since however, the conical pins 106, 108 are guided linearly on the sliders 110, 112, only one possible degree of freedom of the movement is obtained as a result of the centrifugal force. An improvement of the mechanism compared with conventional systems is that the articulation point of the coupling rods 124, 126 is positioned on the rotatably mounted disk 118 in the closed state such that a very low effective lever arm, ideally lever arm=0, is obtained with respect to the pivot point of the disk 118. This has the result that due to the centrifugal force, a very small torque is exerted on the disk 118 whereas the effective lever arm of the prestressed spring 120 on the disk 118 is large. This has the advantage that a very rigid connection of positioning pins 106, 108 and microtiter plate 302 can be achieved with a very small spring force. Despite this rigid connection, in the opened state the mechanism can be equipped with the microtiter plate in a forceless manner. Another advantage of this mechanism lies in the centering of the microtiter plate 302 with regard to the carrier. The manufacturing tolerances of length and width of the microtiter plates 302 therefore do not influence the position of the wells in relation to the center of the carrier 104.

One improvement is that now all the elements lie in one plane and as a result the overall height of the mechanism is substantially reduced. In addition, due to the conical pins 106, 108, it is relatively easily possible to adapt the mechanism to other objects and geometries.

Figure 12:
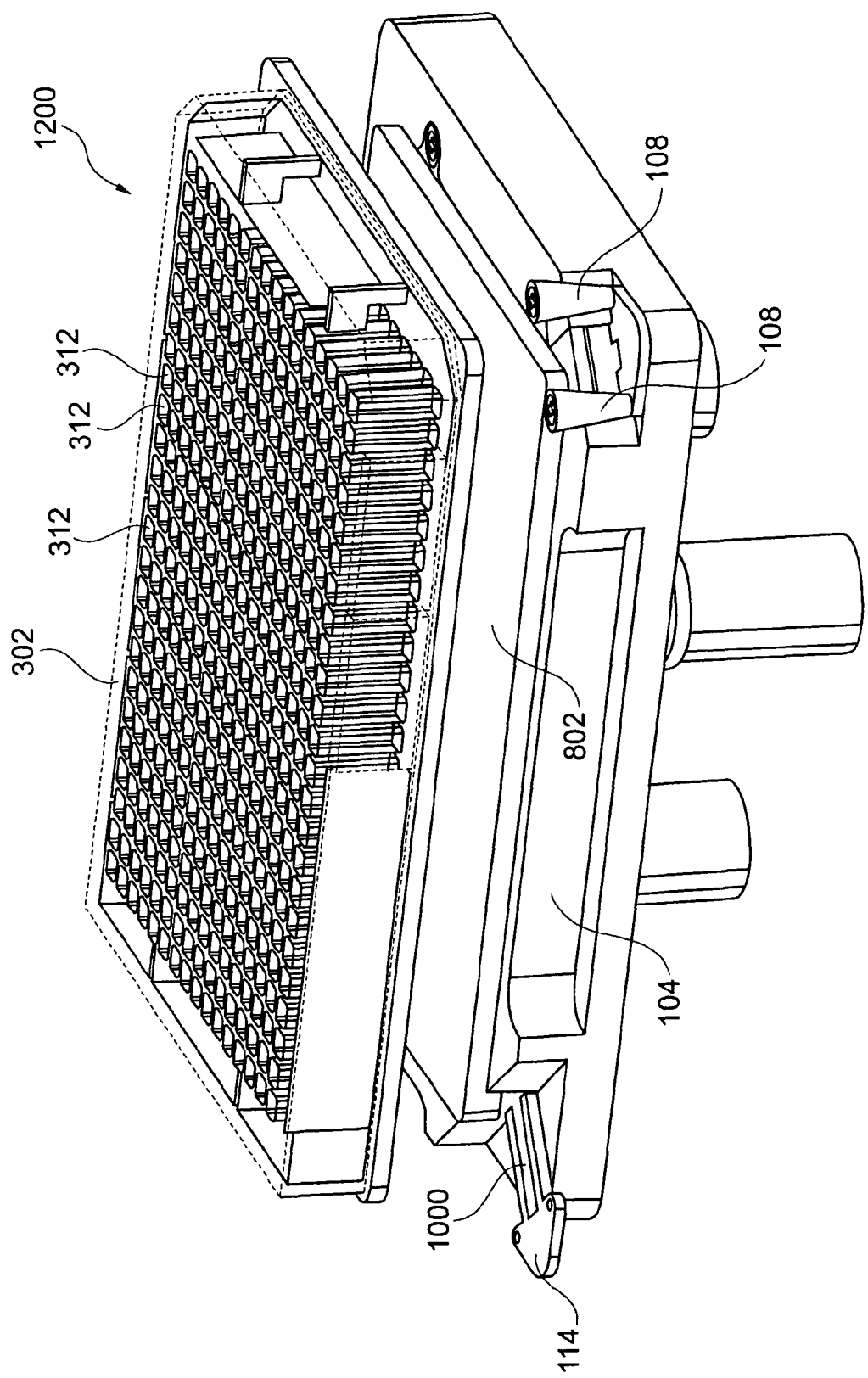
FIG. 12 shows a positioning apparatus according to another exemplary embodiment of the invention with a microtiter plate.
Figure 13:
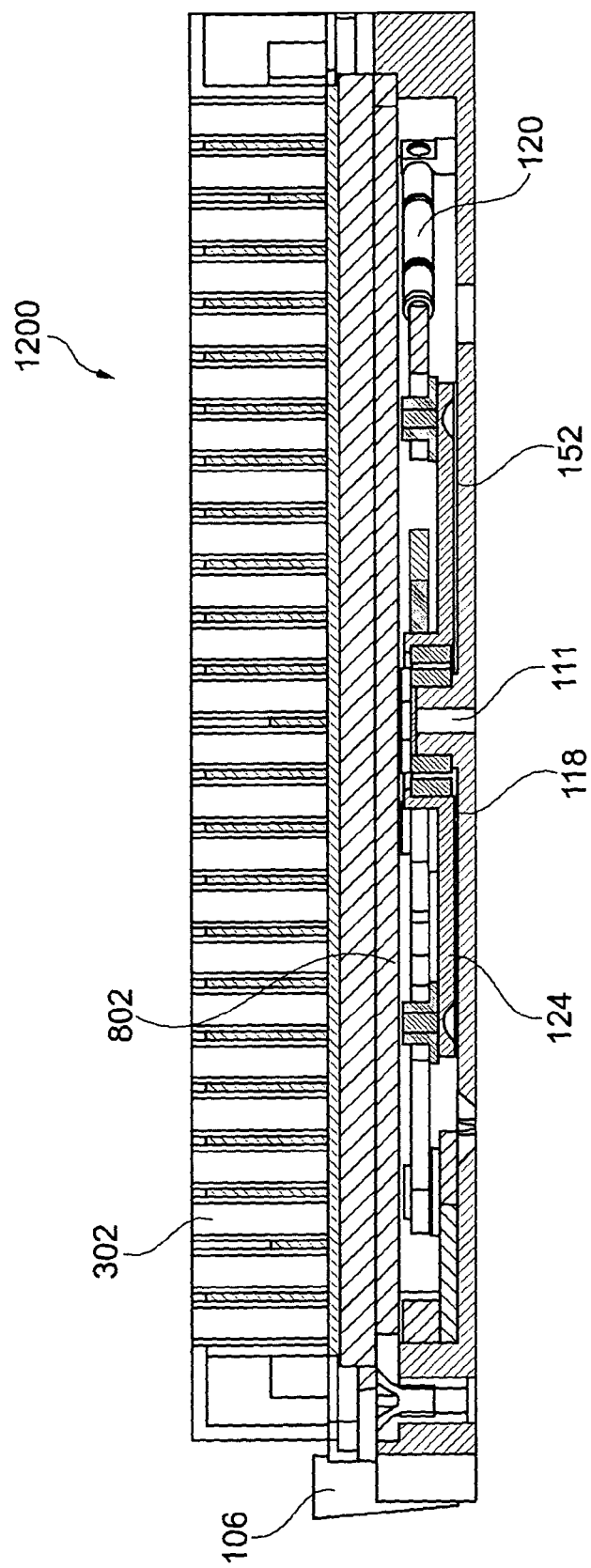
FIG. 13 shows a cross-section through an interior of a carrier body of the positioning apparatus according to FIG. 12 and therefore illustrates a section through a mechanism with an inserted flat-bottom microtiter plate.

FIG. 12 shows a sample handling device 1200 according to yet another exemplary embodiment of the invention. FIG. 13 shows a section through the basic mechanism with inserted flat-bottom microtiter plate 302.

Figure 14:
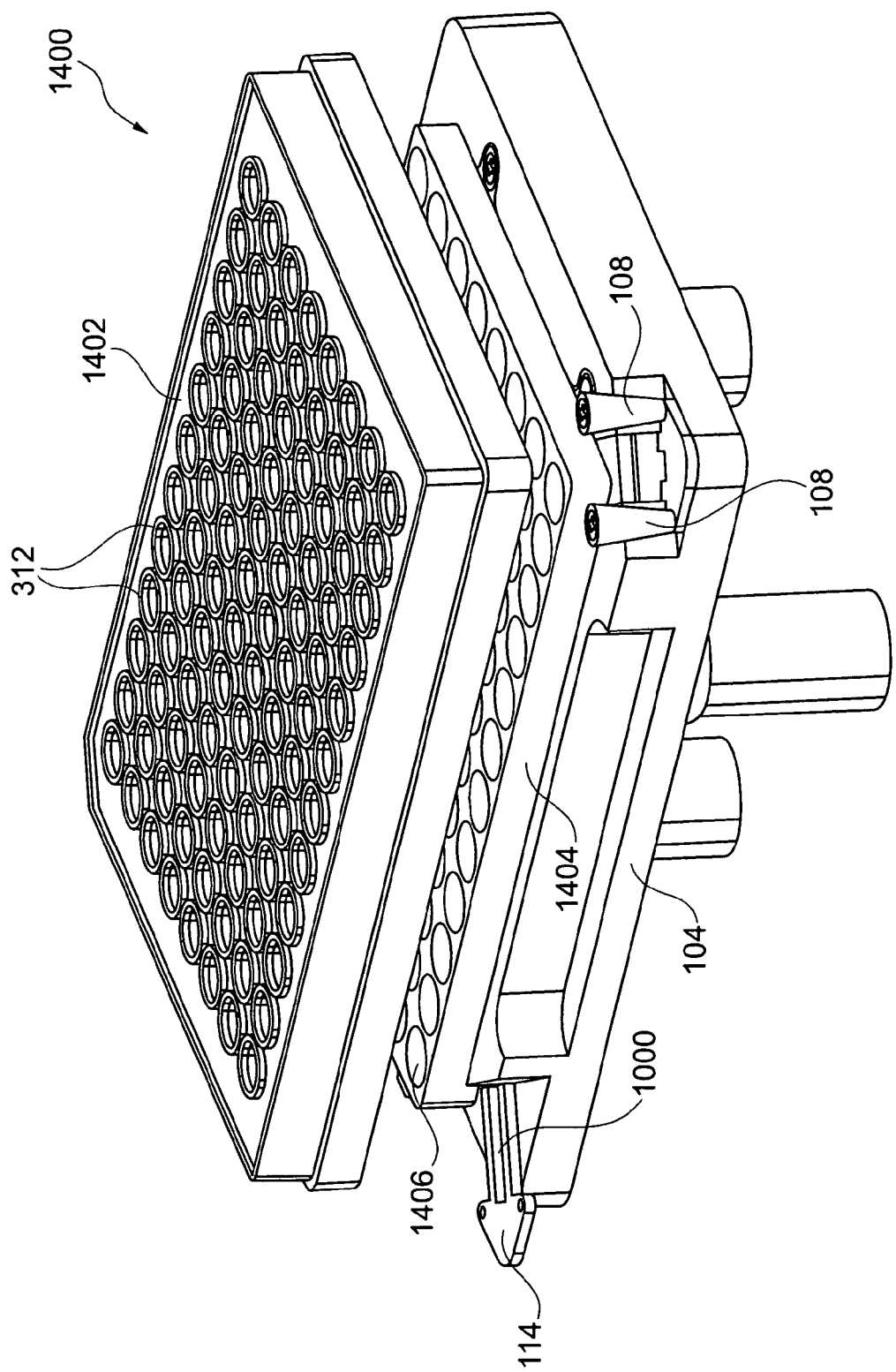
FIG. 14 shows the positioning apparatus according to FIG. 12 and FIG. 13 and in particular a mechanism with a round-bottom microtiter plate and adapted adapter plate.

FIG. 14 shows a sample handling device 1400 according to yet another exemplary embodiment of the invention in which a microtiter plate 1402 with a structured underside (see FIG. 15) is placed on a correspondingly shaped adapter plate 1404.

Accordingly, an upper side of the adapter plate 1404 according to FIG. 14 is provided with a topography such that projections 1500 on the underside of the microtiter plate 1402 can engage seamlessly in wells 1406 of the adapter plate 1404.

Figure 16:
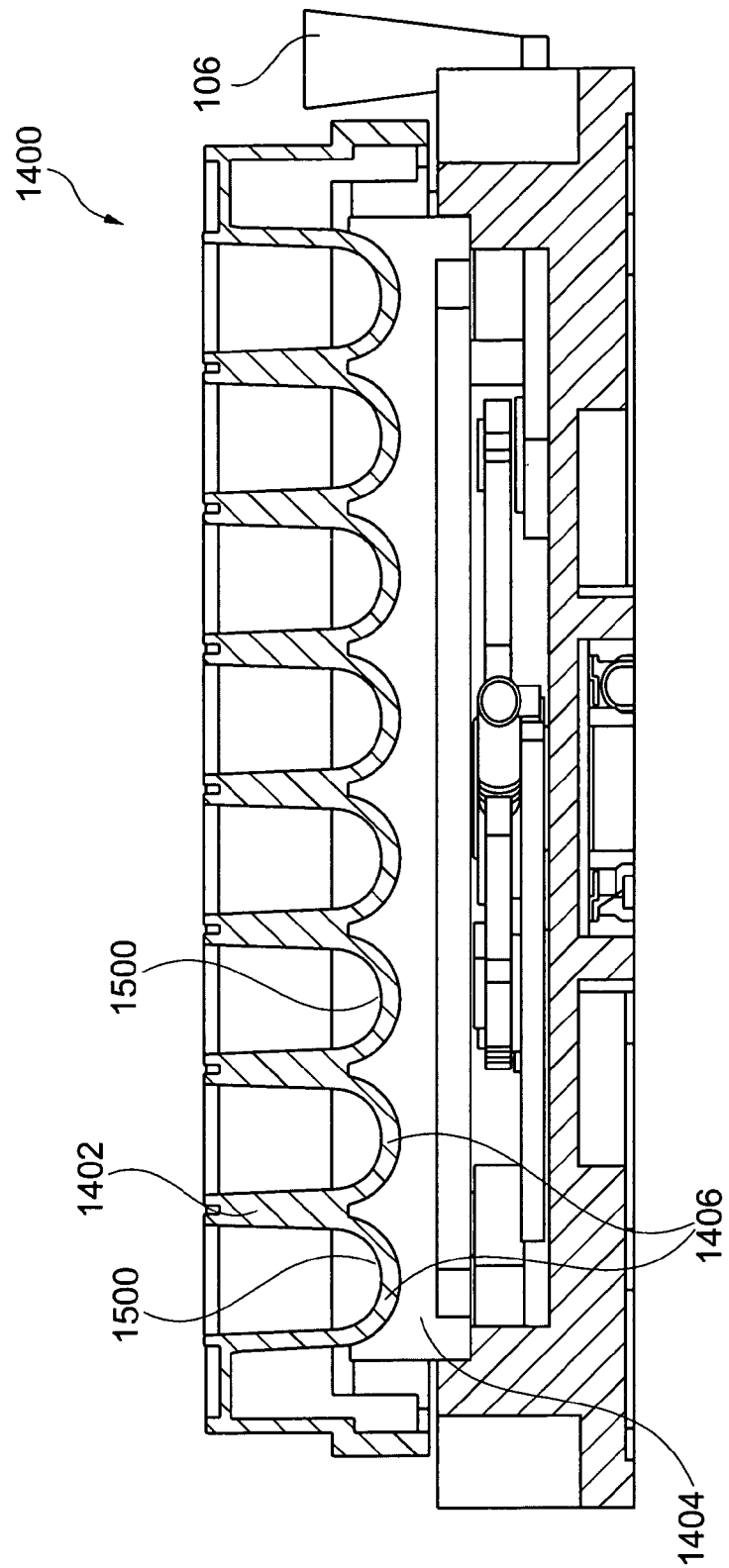
FIG. 16 shows a section of the positioning apparatus according to FIG. 12 to FIG. 15 through a mechanism with inserted round-bottom microtiter plate.

FIG. 16 shows a view in which the round-bottom microtiter plate 1402 is placed seamlessly on the adapter surface 1404.

Figure 17:
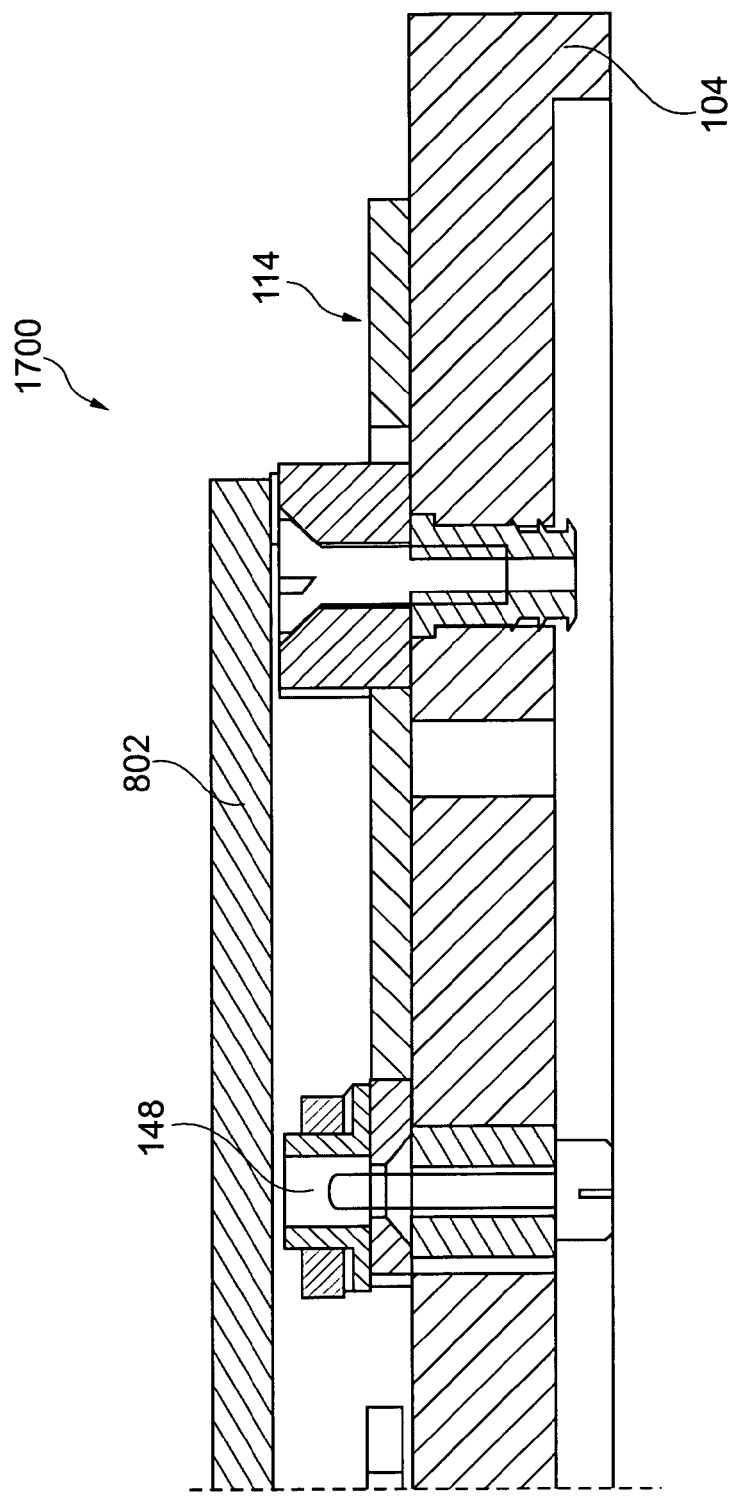
FIG. 17 shows a section along the line of intersection A-A according to FIG. 9.

Again with reference to FIG. 9, a line of intersection A-A is shown there along which the section 1700 illustrated in FIG. 17 is shown. The configuration of the actuating element 114 can also be seen in detail from FIG. 17.

Figure 18:
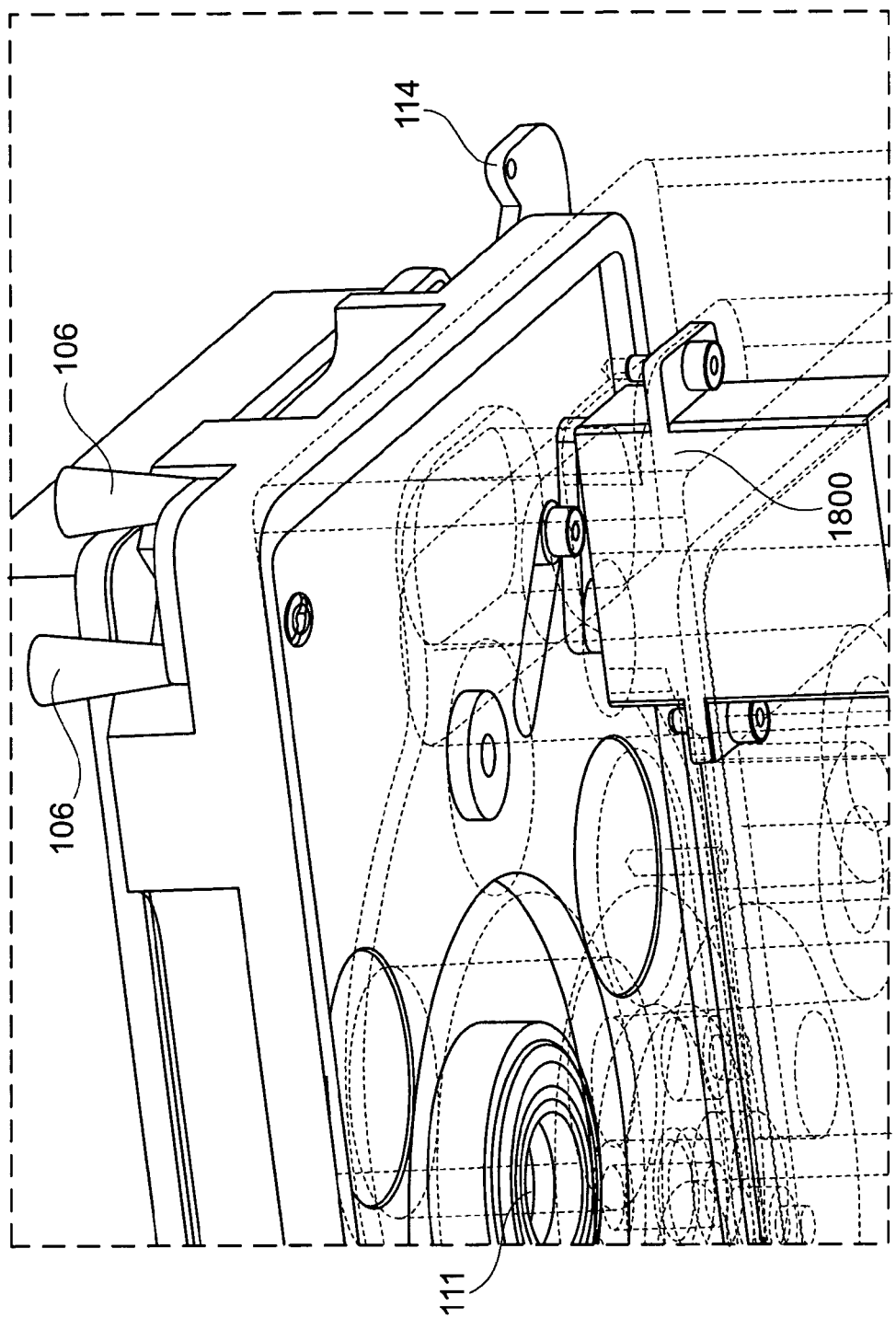
FIG. 18 shows a partial view of the positioning apparatus according to FIG. 12 to FIG. 17 in which the position of a servo motor mechanism is closed.
Figure 19:
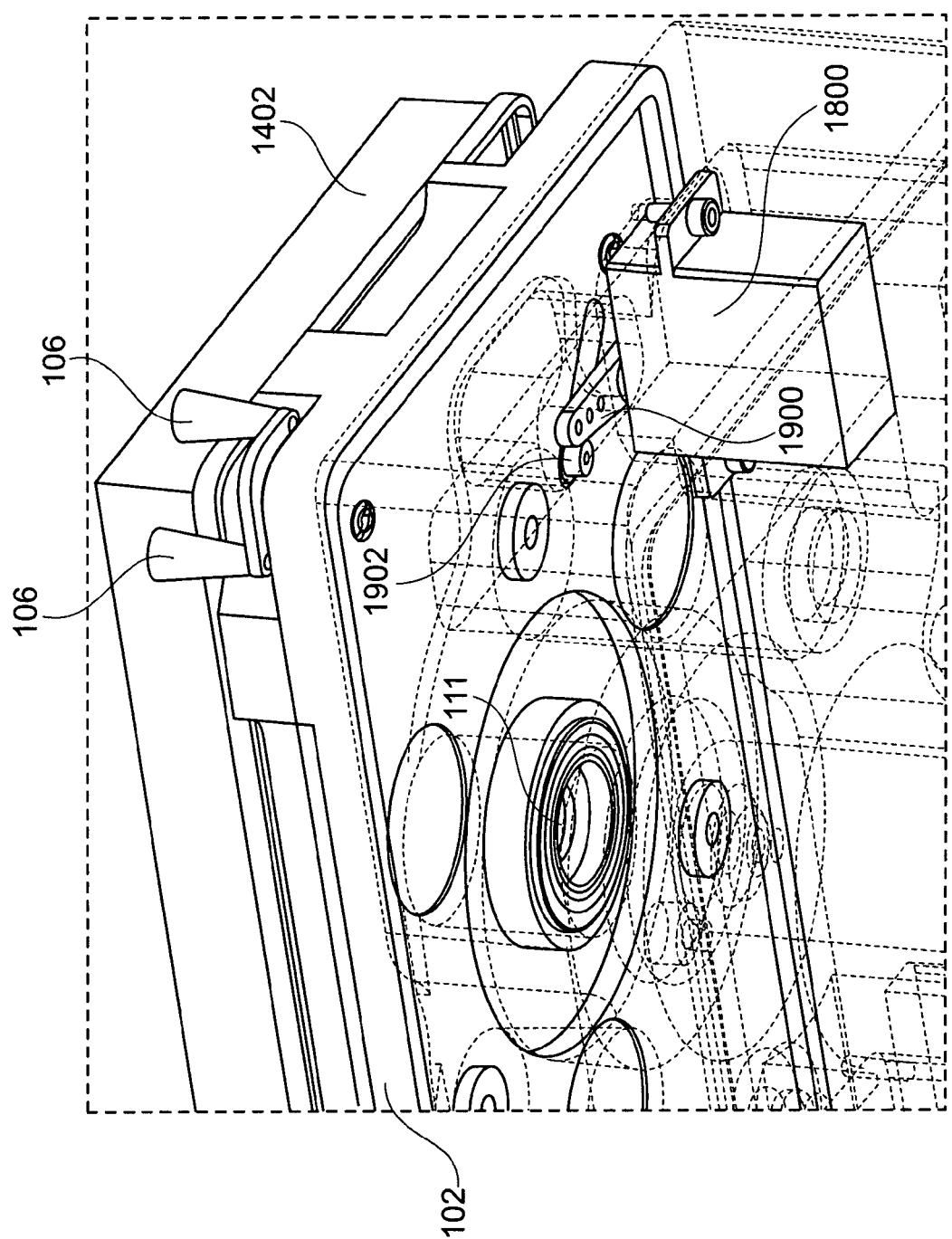
FIG. 19 shows the position of the servo motor open.

FIG. 18 shows a position of a servomotor mechanism in a closed state while FIG. 19 shows the corresponding situation for an open state. This servo is characterized by reference number 1800.

Figure 20:
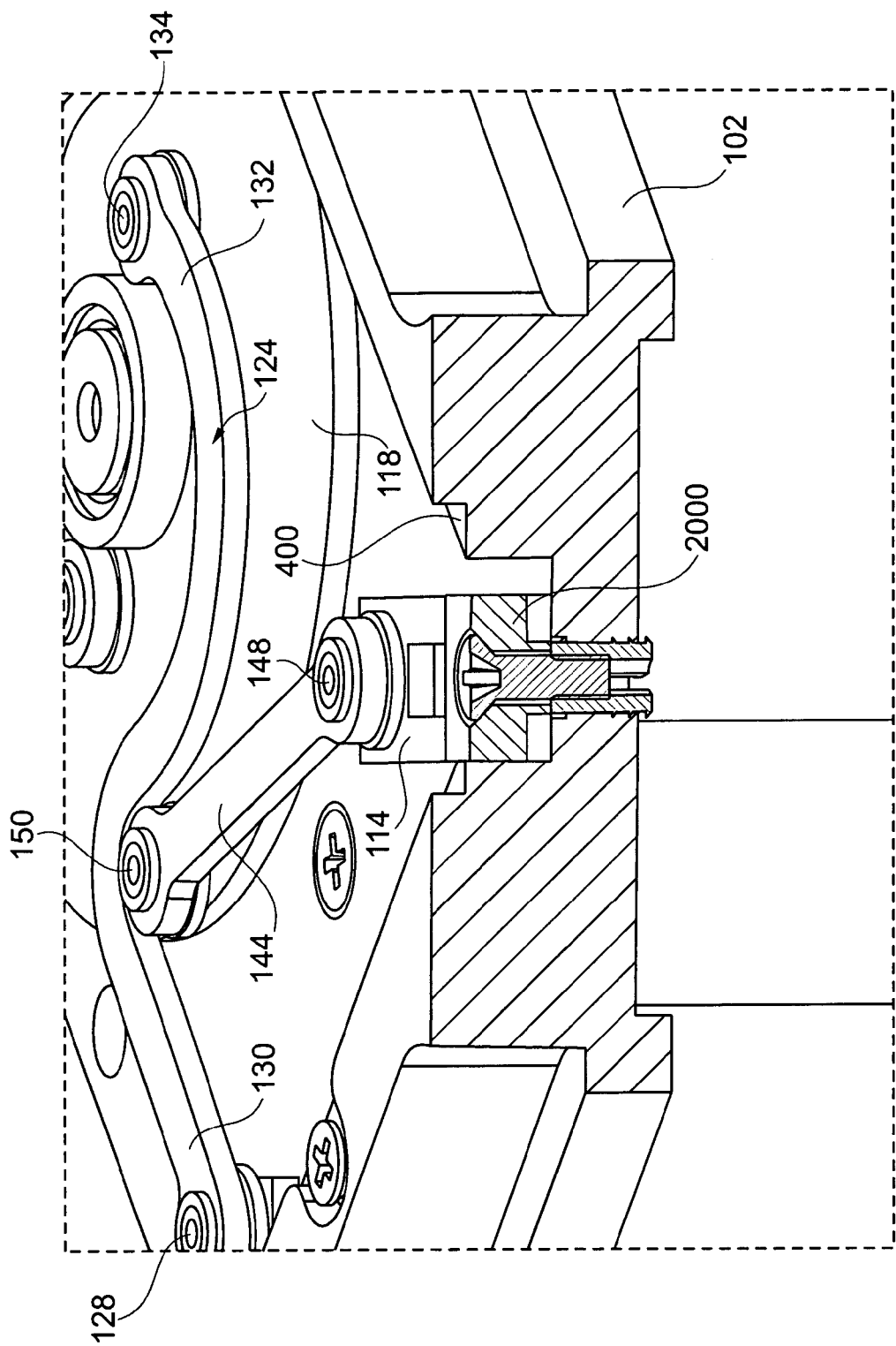
FIG. 20 shows a sectional view through a linear guide of the mechanism.

FIG. 19 shows a lever arm 1900 which presses against a pin or screw head 1902. The linear guidance of the slider 114 is accomplished via a groove in these sliders using a groove block 2000 which is shown in FIG. 20.

An functioning mode of the exemplary embodiments from FIG. 12 to FIG. 20 is described once again hereinafter.

FIG. 12 shows a microtiter plate 392 having a flat bottom. FIG. 13 shows a section through the mechanism with inserted flat-bottom microtiter plate 1402. The adapter plate 802 which enables a temperature control of the microtiter plate 1402 fixes the microtiter plate 1402 only vertically. The microtiter plate 1402 remains movable horizontally without the action of the positioning pieces 106, 108.

Figure 15:
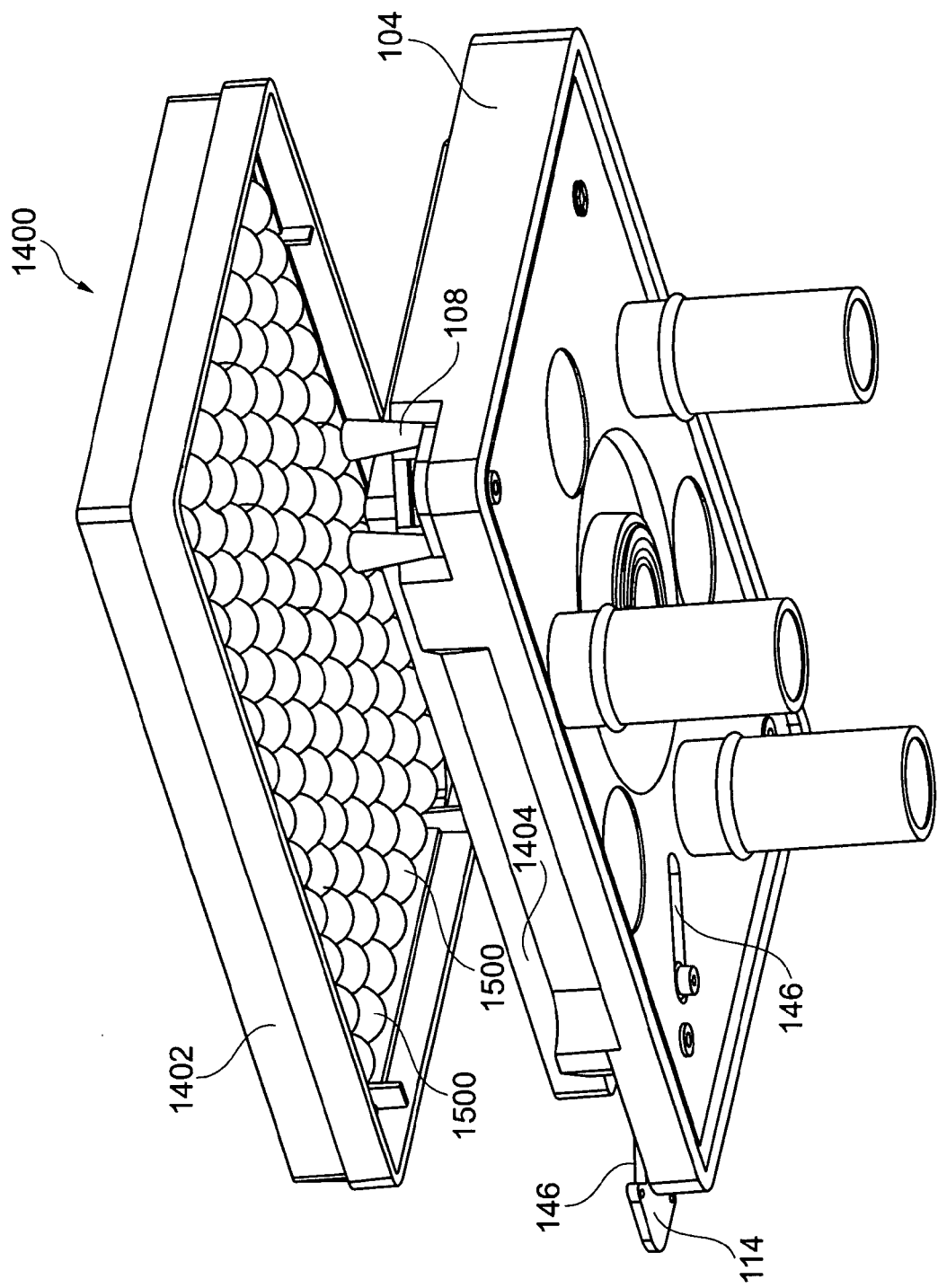
FIG. 15 shows a mechanism with round-bottom microtiter plate and adapted adapter plate from below in accordance with the positioning apparatus according to FIG. 12 to FIG. 14.

FIG. 14 shows the mechanism with a microtiter plate having a round bottom and an adapter plate 1404 adapted to this shape. FIG. 15 shows the shape of the bottom of the microtiter plate 1402. FIG. 16 shows a section through the mechanism with inserted microtiter plate 1402. It can be seen here that when using a microtiter plate having a profiled bottom without the action of positioning pieces 106, 108, a certain horizontal securing of the microtiter plate 1402 is accomplished.

The mechanism is either actuated manually by actuating the slider 114 or by an electrical actuator. These facts of the matter are shown in FIG. 18 to FIG. 20. The automated actuation can be accomplished by a servo 1800 having a lever arm 1900 attached to its shaft, which presses against a pin or here screw head 1902. As a result, this is displaced inside the groove and the mechanism thereby opened. In the closed state lever arm 1900 and screw head 1902 do not contact. The screw head is connected to the slider 114 via a thread and a joint.

The linear guidance of the three sliders is accomplished via a groove in these sliders and a groove block 2000. In FIG. 20 the functioning mode is shown for the example of a slider. The linear guidance of the other sliders functions similarly.

The conical pins 106, 108 are fastened on the sliders by screwing. As a result, these elements can be exchanged by the user in a particularly simple manner. The mechanism can thus be adapted to different geometries and different base heights of the microtiter plate rapidly and uncomplicatedly.

Figure 21:
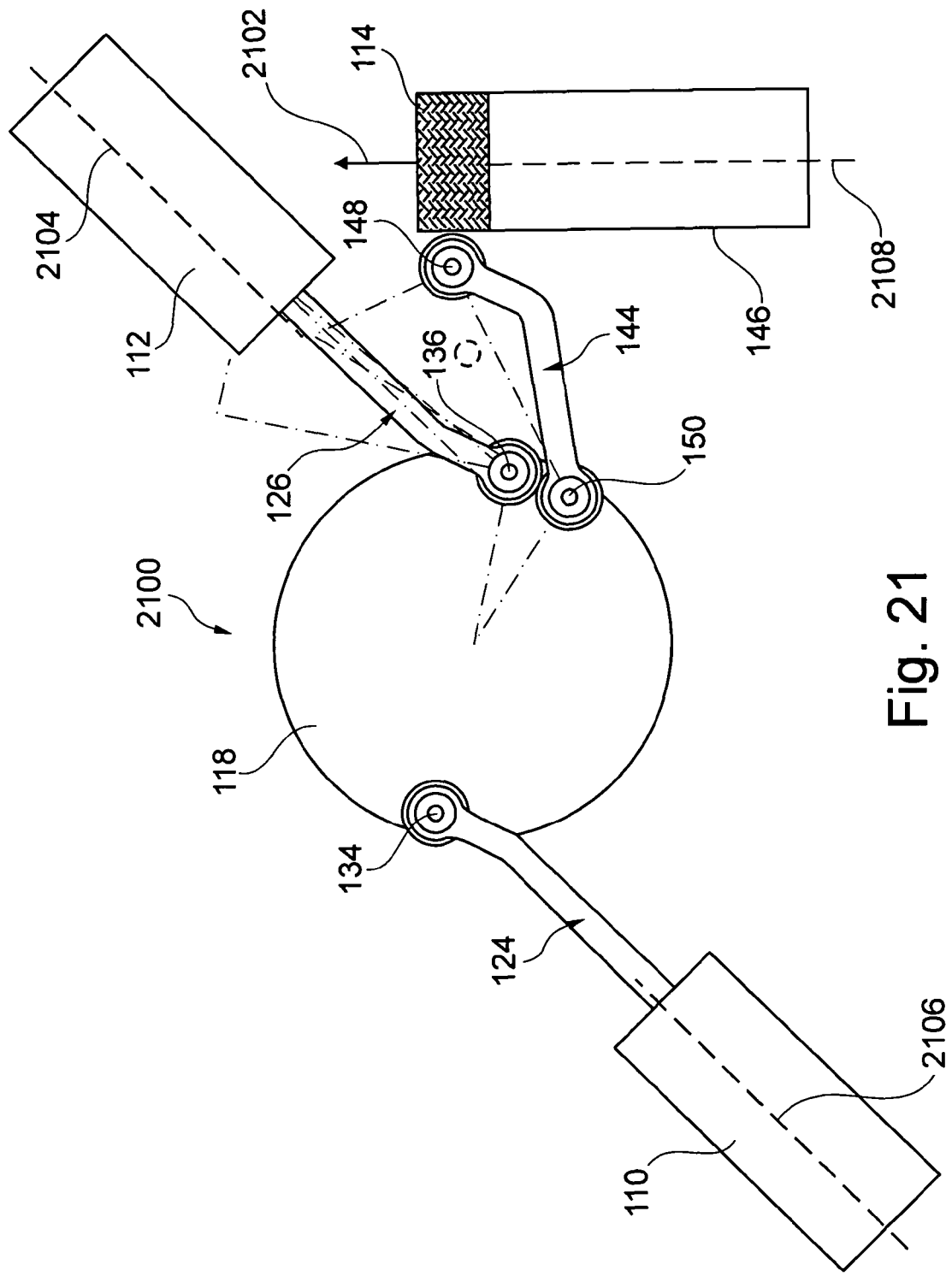
FIG. 21 and FIG. 22 show in plan view schematic diagrams of a positioning device according to one exemplary embodiment of the invention where in an operating state shown in FIG. 21, a sample carrier plate can be clamped between positioning stops by actuating an actuating device and where in an operating state shown in FIG. 22, the sample carrier plate is shaken, clamped between positioning stops, without the shaking force undesirably setting the actuating device in motion.
Figure 22:
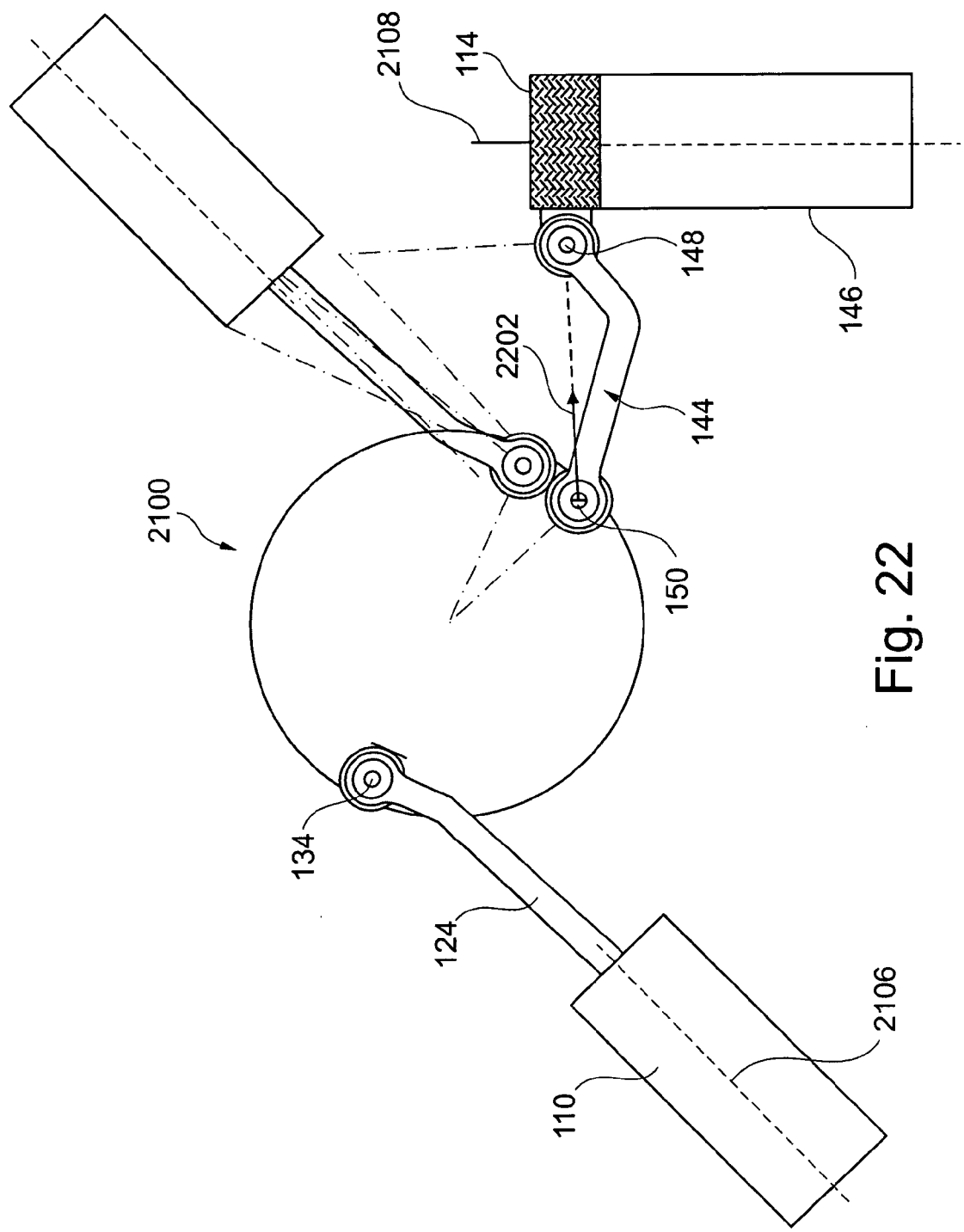

FIG. 21 and FIG. 22 show in plan view schematic diagrams of a positioning device 2100 according to one exemplary embodiment of the invention. The arrangement can be configured similarly to that shown in FIG. 1 so that only the components relevant for explaining the functioning principle of a movement block for preventing any movement of an actuating device 114 as a result of a shaking of a sample carrier plate are shown in FIG. 21 and in FIG. 22. If the positioning stops are located in opposite corner regions of the positioning device 2100, the corresponding forces should be suitably deflected, for example, by using suitable coupling rod geometries with respect to the schematic diagram in FIG. 21 and FIG. 22.

In an operating state shown in FIG. 21, a sample carrier plate, not shown, is inserted between positioning stops, not shown, by actuating the actuating element 114. If the actuating element 114 is pushed upward in the direction of an arrow 2102 according to FIG. 21, the coupling rod 144 is thereby tilted, leading to a twisting of the force transmitting disk 118. As a result, the coupling rods 124, 126 are also twisted, with the result that sliders of the linear displacement devices 110, 112 are displaced along linear displacement directions 2104, 2106 and consequently positioning stops are pressed outward.

In an operating state shown in FIG. 22 the sample carrier plate is already clamped between the positioning stops and is shaken by means of a shaking device (not shown) without the shaking force undesirably setting the actuating device 114 in motion. This is accomplished using a force transmission mechanism which is described hereinafter.

The actuating element 114 and the force transmitting disk 118 functioning as force transmitting element are coupled by means of the coupling rod 144 in such a manner that a shaking force of the shaking device is transmitted to the actuating element 114 in such a manner that despite the action of the transmitted shaking force, the actuating element 114 remains in the rest position according to FIG. 22, i.e. does not move up or down according to FIG. 22. The actuating element 114 and the force transmitting disk 118 are coupled by means of the coupling rod 144 in such a manner that in the operating state according to FIG. 22 the coupling rod 144 couples in the shaking force, cf. reference number 2202, perpendicular to a displacement direction 2108 of the actuating element 114.

In an orthogonal position between the coupling rod 144 and the displacement direction 2108 according to FIG. 22, no shaking force component can lead to a movement of the actuating element 114 so that this type of force transmission advantageously blocks the movement. In the other force transmission direction, i.e. from the actuating element 114 to the linear guide devices 110, 112, on the other hand a force transmission leading to a movement can take place since the coupling rods 124, 126 are not perpendicular (but even approximately parallel) to the linear displacement directions 2104, 2106.

In the closed state according to FIG. 22, an angle of almost 90° can be achieved between coupled-in shaking force 2202 and displacement direction 2108. The system is then so well clamped that springs could also be omitted. The system can almost not be pushed open over the corners and also reliably withstands very high shaking speeds.

In addition, it should be noted that "comprising" does not exclude any other elements or steps and "an" or "a" does not exclude a plurality. It should also be noted that features or steps which have been described with reference to one of the above exemplary embodiments can also be used in combination with other features or steps of other exemplary embodiments described above. Reference numbers in the claims are not to be construed as a restriction.

What is claimed is:

1. An apparatus for positioning a sample carrier plate, wherein the apparatus comprises:
    a main body for receiving the sample carrier plate;
    positioning stops, which are disposed in diagonally opposing first corner regions of the main body and are prestressed for clamping the sample carrier plate and mounted displaceably;
    an actuating device which is disposed at the main body and is adapted such that by actuating the actuating device, the positioning stops can be transferred between an operating state engaging the sample carrier plate and an operating state releasing the sample carrier plate;
    a force transmitting element which is adapted to transmit an actuating force from the actuating device to the positioning stops, the force transmitting element comprises a rotatably mounted coupling disk, wherein the rotatably mounted coupling disk is coupled to the actuating device and the positioning stops,
    a plurality of first coupling rods, each of which is coupled to the respective positioning stop and to the rotatably mounted coupling disk, wherein the first coupling rods are pivotably connected in an articulated manner by a first rotatable connecting element to the rotatably mounted coupling disk,
    a second coupling rod by which the actuating device is pivotably coupled to the rotatably mounted coupling disk, wherein the second coupling rod is pivotably connected in an articulated manner by a second rotatable connecting element to the rotatably mounted coupling disk and is pivotably connected in an articulated manner by a third rotatable connecting element to the actuating device.

2. The apparatus of claim 1, wherein the main body comprises an adapter plate for receiving the sample carrier plate, wherein the adapter plate is a flat adapter plate for positive receipt of a flat sample carrier plate, and wherein the main body has a recess in which the adapter plate can be inserted so that it ends flush on an upper side.

3. The apparatus of claim 2, wherein the adapter plate has a surface structure which is adapted for the positive receipt of a sample carrier plate having a surface structure complementary to the surface structure of the adapter surface.

4. The apparatus of claim 1, wherein the positioning stops are disposed exclusively at two opposite first corner regions of the main body, wherein the positioning stops in each first corner region are formed by means of two stop elements having two mutually perpendicular stop lines for placement on a rectangular sample carrier plate, wherein the positioning stops in each first corner region are formed by means of two stop elements having a round cross-section for placement on the sample carrier plate.

5. The apparatus of claim 1, wherein each of the positioning stops is assigned a first linear guide element in which the respective positioning stop is mounted linearly displaceably, wherein the first linear guide elements are oriented such that the positioning stops are mounted displaceably parallel to one another, wherein the first linear guide elements are adapted such that the positioning stops are mounted displaceably and parallel offset with respect to a diagonal of the main body.

6. The apparatus of claim 1, wherein the actuating device comprises a slider for manual actuation by a user, wherein the slider has a gripping piece having an arrow-shaped end section.

7. The apparatus of claim 1, wherein the actuating device comprises a coupling piece for coupling to an electrical actuator device, the apparatus further comprising the electrical actuator device, which engages in the coupling piece for transmission of an electrical actuating force to the force transmitting element, wherein the electrical actuator device comprises a drive shaft and a lever arm disposed thereon, which acts on a force transmitting pin for transmission of the electrical actuating force, which pin is disposed movably in a linear guide groove of the actuating element.

8. The apparatus of claim 1, further comprising a prestressing device disposed adjacent to a third corner region of the main body, which is adapted for transmitting a prestress, in particular a tensile prestress, to the force transmitting element, wherein optionally the prestressing device comprises a spring, one end of which is fastened to the main body and the other end of which is coupled to the force transmitting element, wherein further the second corner region lies opposite the third corner region.

9. The apparatus of claim 8, wherein the rotatably mounted coupling disk is coupled to the prestressing device, wherein the first coupling rods are coupled in an articulated manner to the rotatably mounted coupling disk and are connected to the respective positioning stop in an articulated manner by means of a respective first linear guide, wherein the first coupling rods comprise a rectilinear section, which adjoins the respective first linear guide and comprise a bent section, which is guided around the rotatably mounted coupling disk.

10. The apparatus of claim 1, wherein the second coupling rod is connected in an articulated manner to the rotatably mounted coupling disk and is connected in an articulated manner to the actuating device by means of a second linear guide, wherein the second coupling rod is rectilinear, wherein one of the first coupling rods and the second coupling rod are connected to the rotatably mounted coupling disk by means of a common connecting element.

11. The apparatus of claim 9, further comprising a third coupling rod, by which the prestressing device is coupled to the rotatably mounted coupling disk, wherein the third coupling rod is connected in an articulated manner to the rotatably mounted coupling disk, wherein the third coupling rod is rectilinear, wherein one of the first coupling rods and the third coupling rod are connected by means of a common connecting element to the rotatably mounted coupling disk, wherein the first coupling rods, the second coupling rod, and the third coupling rod are disposed in a coplanar manner, wherein the first coupling rods, the second coupling rod, and the third coupling rod are mounted on a circular top surface of the coupling disk, wherein each of the first coupling rods are connected by means of an appurtenant connecting element on the rotatably mounted coupling disk and the connecting elements of the first coupling rods are mounted radially further inward on the coupling disk than the connecting elements of the other coupling rods.

12. The apparatus of claim 8, wherein the prestressing device and the actuating device are mounted in a coplanar manner.

13. A method for positioning a sample carrier plate, wherein the method comprises:
receiving the sample carrier plate on a main body of a device;
clamping the sample carrier plate on prestressed and displaceably mounted positioning stops, which are disposed in diagonally opposite first corner regions of the main body;
actuating an actuating device disposed at the main body for transferring the positioning stops between an operating state engaging the sample carrier plate and an operating state releasing the sample carrier plate; and
transmitting an actuating force from the actuating device to the positioning stops by means of a rotatably mounted coupling disk,
wherein the rotatably mounted coupling disk is coupled to the actuating device and the positioning stops, and
wherein a plurality of first coupling rods are coupled to the respective positioning stop and to the rotatably mounted coupling disk, wherein the first coupling rods are pivotably connected in an articulated manner by a first rotatable connecting element to the rotatably mounted coupling disk,
wherein the actuating device is coupled to the rotatably mounted coupling disk by a second coupling rod;
wherein the second coupling rod is pivotably connected in an articulated manner by a second rotatable connecting element to the rotatably mounted coupling disk and is connected in an articulated manner by a third rotatable connecting element to the actuating device.

* * * * *